United States Patent
Lachenbruch et al.

(10) Patent No.: US 10,426,396 B2
(45) Date of Patent: Oct. 1, 2019

(54) PRESSURE ULCER DETECTION SYSTEMS AND METHODS

(71) Applicant: Hill-Rom Services, Inc., Batesville, IN (US)

(72) Inventors: Charles A. Lachenbruch, Batesville, IN (US); David L. Ribble, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 366 days.

(21) Appl. No.: 15/040,170

(22) Filed: Feb. 10, 2016

(65) Prior Publication Data

US 2017/0224271 A1    Aug. 10, 2017

(51) Int. Cl.
| | |
|---|---|
| *A61B 5/103* | (2006.01) |
| *A61B 5/00* | (2006.01) |
| *A61G 12/00* | (2006.01) |
| *A61B 6/00* | (2006.01) |
| *A61B 90/30* | (2016.01) |
| *A61B 90/00* | (2016.01) |

(52) U.S. Cl.
CPC ............ *A61B 5/447* (2013.01); *A61B 5/0075* (2013.01); *A61B 5/7282* (2013.01); *A61B 5/746* (2013.01); *A61G 12/00* (2013.01); *A61B 2090/306* (2016.02); *A61B 2090/3614* (2016.02); *A61B 2576/00* (2013.01)

(58) Field of Classification Search
CPC .............................. A61B 5/0064; A61B 5/447
USPC .................................................. 600/476, 587
See application file for complete search history.

(56) References Cited

U.S. PATENT DOCUMENTS

| | | | |
|---|---|---|---|
| 7,155,273 | B2 | 12/2006 | Taylor |
| 8,073,535 | B2 | 12/2011 | Jung et al. |
| 8,095,706 | B2 | 1/2012 | Sprigle et al. |
| 2004/0054303 | A1 | 3/2004 | Taylor |

(Continued)

FOREIGN PATENT DOCUMENTS

| | | |
|---|---|---|
| WO | 2008039539 A2 | 4/2008 |
| WO | 2011113070 A1 | 9/2011 |

OTHER PUBLICATIONS

EP Search Report for EP Application 13168435.9; dated Aug. 2, 2013; Place of Search—The Hague; Date of Completion of the Search—Jul. 25, 2013; Marteau, Frederic.

(Continued)

*Primary Examiner* — Jon Eric C Morales

(74) *Attorney, Agent, or Firm* — Kenneth C. Baran

(57) ABSTRACT

A pressure ulcer detection system includes a support surface assembly including a transparent window, a signal generator/receiver, and an optical fiber embedded at least in part in the support surface assembly. The fiber conveys outgoing radiation from the signal generator/receiver to the window thereby illuminating a tissue site which overlies the window and conveys incoming radiation reflected from the tissue site and through the window back to the generator/receiver. The system also includes a controller in communication with the signal generator/receiver. The controller comprises a processor adapted to assess health status of tissue at the tissue site based on a property of at least one of the outgoing radiation and the incoming radiation, and to communicate an outcome of the assessment to a destination.

9 Claims, 27 Drawing Sheets

(56) References Cited

U.S. PATENT DOCUMENTS

| | | |
|---|---|---|
| 2010/0091104 A1 | 4/2010 | Sprigle et al. |
| 2010/0140461 A1 | 6/2010 | Sprigle et al. |
| 2012/0029879 A1 | 2/2012 | Sing et al. |
| 2012/0035469 A1 | 2/2012 | Whelan et al. |
| 2012/0138801 A1 | 6/2012 | Vanderpohl |
| 2013/0310696 A1* | 11/2013 | Ribble ................ A61B 5/0064 600/476 |
| 2014/0088380 A1 | 3/2014 | Sprigle et al. |

OTHER PUBLICATIONS

Journal of Biomedical Optics, 046007, Jul./Aug. 2010, vol. 15(4); Principal component model of multispectral data for near real-time skin chromophore mapping.

Non-Invasive Erythema Detection Using Spectral Imaging Publication; Published 2005; RESNA 28th Annual Conference—Atlanta, Georgia; Sharon Eve Sonenblum, MS; Stephen Sprigl PhD, PT; Leanne West, MS; Jack Wood, MS; Georgia Institute of Technology.

Single Sensor That Outputs Narrowband Multispectral Images; Kong, L., Yi, D., Sprigle, S., Yang, F., Wang, C., Liu, F., Adibi, A., and Tummala, R.; Paper 09298LRR received Jul. 21, 2009; revised manuscript received Nov. 2, 2009; accepted for publication Nov. 9, 2009; published online Jan. 7, 2010; Journal of Biomedical Optics, 010502-1-3, Jan./Feb. 2010, vol. 15(1).

Detecting Early Stage Pressure Ulcer on Dark Skin Using Multispectral Imager; Yi, D., Kong, L., Sprigle, S., Wang, F., Wang, C., Liu, F., Adibi, A., and Tummala, R.; Biomedical Vibrational Spectroscopy IV; Advances in Research and Industry, edited by Annita Mahadevan-Jansen, Wolfgang Petrich, Proc. of SPIT vol. 7560; 75600U-1-8.

Handheld Erythema and Bruise Detector; Kong, L., Sprigle, S., Duckwork, M.G., Yi, D., Caspall, J.J., Wang, J., Zhao, F.; Medical Imaging 2008; Computer-Aided Diagnosis, edited by Maryellen L. Giger, Nico Karssemeijer; Proc of SPI vol. 6915, 69153K (2008); 69753K-1-7.

Detection of Skin Erythema in Darkly Pigmented Skin Using Multispectral Images; Sprigle, 5., PHD, PT; Zhang, L., PHD; and Duckworth, M., MS; Advances in Skin & Wound Care, vol. 22 No. 4, 172-179; www.woundcarejournal.com.

Testing the Validity of Erythema Detection Algorithms; Brain Riordan, MEBME; Stephen Sprigle, PhD, Pt; Maureen Linden, MSBME; Journal of Rehabilitation Research & Development; Department of Beterans Affairs, Rehabilitation Research & Development Service; vol. 38 No. 1, Jan./Feb. 2001; pp. 13-22.

Response to Rule 69 EPC dated May 23, 2014 for EP Application No. 13168435.9.

Amended Claims in response to Rule 69 dated May 23, 2014 for EP Application No. 13168435.9.

Amended Pages in response to Rule 69 dated May 23, 2014 for EP Application No. 13168435.9.

Communication Pursuant to Article 94(3) EPC for EP Application 13168435.9; dated Nov. 29, 2017.

Response to EP Official Letter for EP Application 13168435.9; dated Mar. 29, 2018.

Claims (clean) for EP Application 1368435.9.

Claims (tracked) or EP Application 1368435.9.

\* cited by examiner

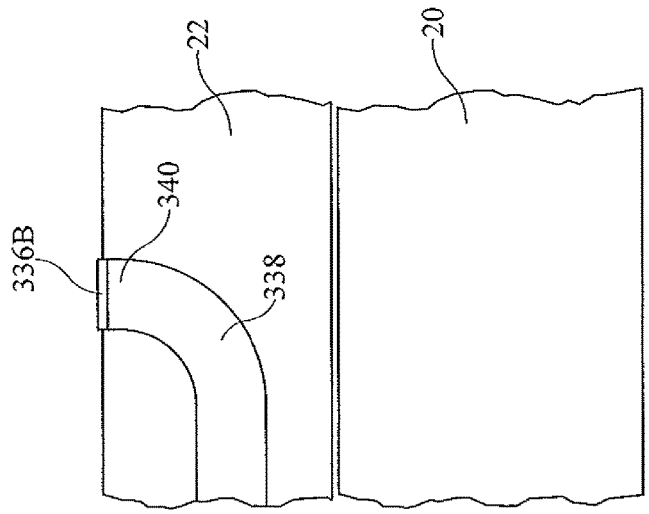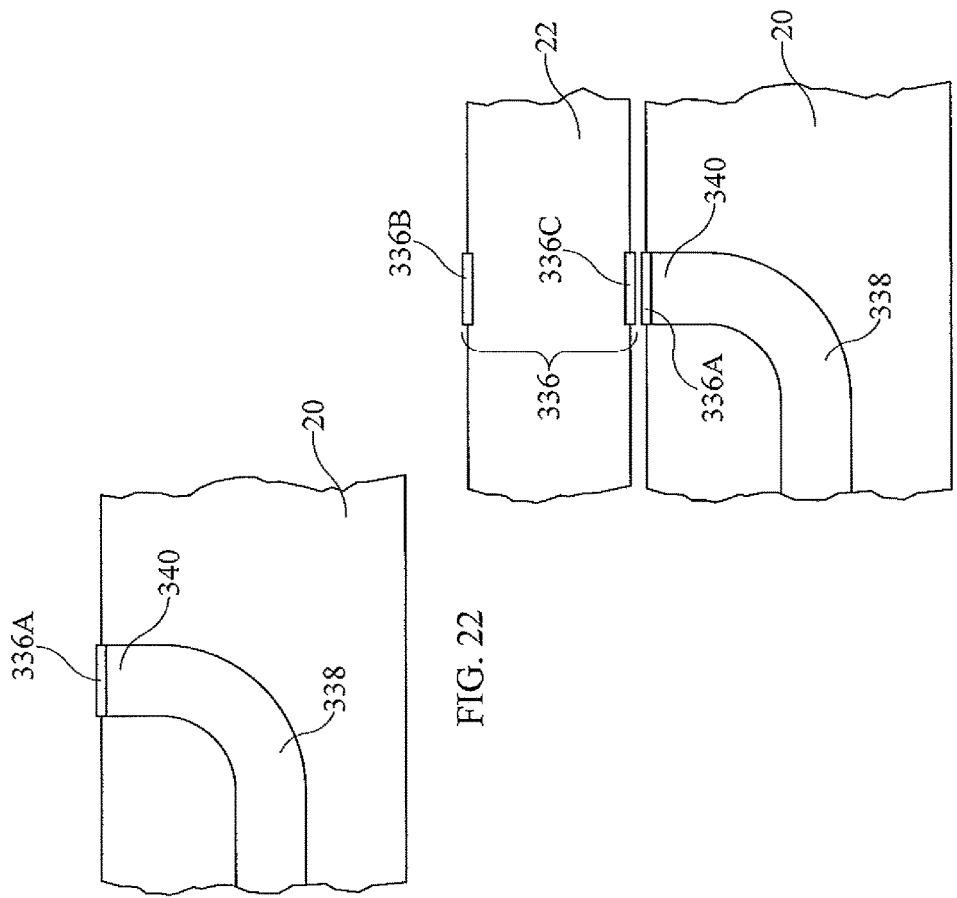

PRESSURE ULCER DETECTION SYSTEMS AND METHODS

CROSS-REFERENCE TO RELATED PATENT APPLICATIONS

This patent application is related to U.S. patent application Ser. No. 13/609,776 filed on Sep. 11, 2012.

BACKGROUND

This application is directed to early detection of skin abnormalities, in particular pressure ulcers. The phrase "early detection" means detecting a pressure ulcer before the pressure ulcer is visually discernible and/or identifiable as a pressure ulcer by visual inspection by a person unaided by anything other than commonplace corrective lenses. Early detection also includes detecting precursors to pressure ulcers. A precursor to a pressure ulcer is a condition that does not qualify as a pressure ulcer but whose presence indicates that a pressure ulcer is likely to develop. Accordingly, the methods and apparatuses described herein for detecting pressure ulcers may also be referred to as methods and apparatuses for predicting pressure ulcers or for detecting precursors to pressure ulcers.

BRIEF SUMMARY

A pressure ulcer detection system comprises a support surface assembly including a transparent window and a signal generator/receiver. An optical fiber is embedded, at least in part, in the support surface assembly. The optical fiber conveys outgoing radiation from the signal generator/receiver to the window thereby illuminating a tissue site which overlies the window. The optical fiber also conveys incoming radiation reflected from the tissue site back through the window back to the generator/receiver. The pressure ulcer detection system also includes a controller in communication with the signal generator/receiver. The controller includes a processor adapted to assess health status of tissue at the tissue site based on a property of at least one of the outgoing radiation and the incoming radiation. The processor is also adapted to communicate an outcome of the assessment to a destination.

An associated method of detecting a pressure ulcer comprises illuminating a target site with incident radiation having at least one property, detecting the at least one property of radiation reflected from the target site, conducting an evaluation to identify whether a dissimilarity is present in the property of the incident radiation relative to the property of the reflected radiation, and communicating an outcome of the evaluation to a destination.

Another associated method of detecting a pressure ulcer comprises illuminating a target site with incident radiation, illuminating a reference site with incident radiation, detecting at least one property of radiation reflected from the target site, detecting at least one property of radiation reflected from the reference site, conducting an evaluation to identify whether a dissimilarity is present in the property of radiation reflected from the target site relative to the property of the radiation reflected from the reference site, and communicating an outcome of the evaluation to a destination.

BRIEF DESCRIPTION OF DRAWINGS

The accompanying drawings illustrate several aspects of the claimed subject matter and, together with the description, serve to explain the principles of the claimed subject matter. In the drawings:

FIG. 22-24 are elevation views showing options for routing an optical fiber through a support surface assembly.

DETAILED DESCRIPTION OF ILLUSTRATIVE EMBODIMENTS

Figure 1:
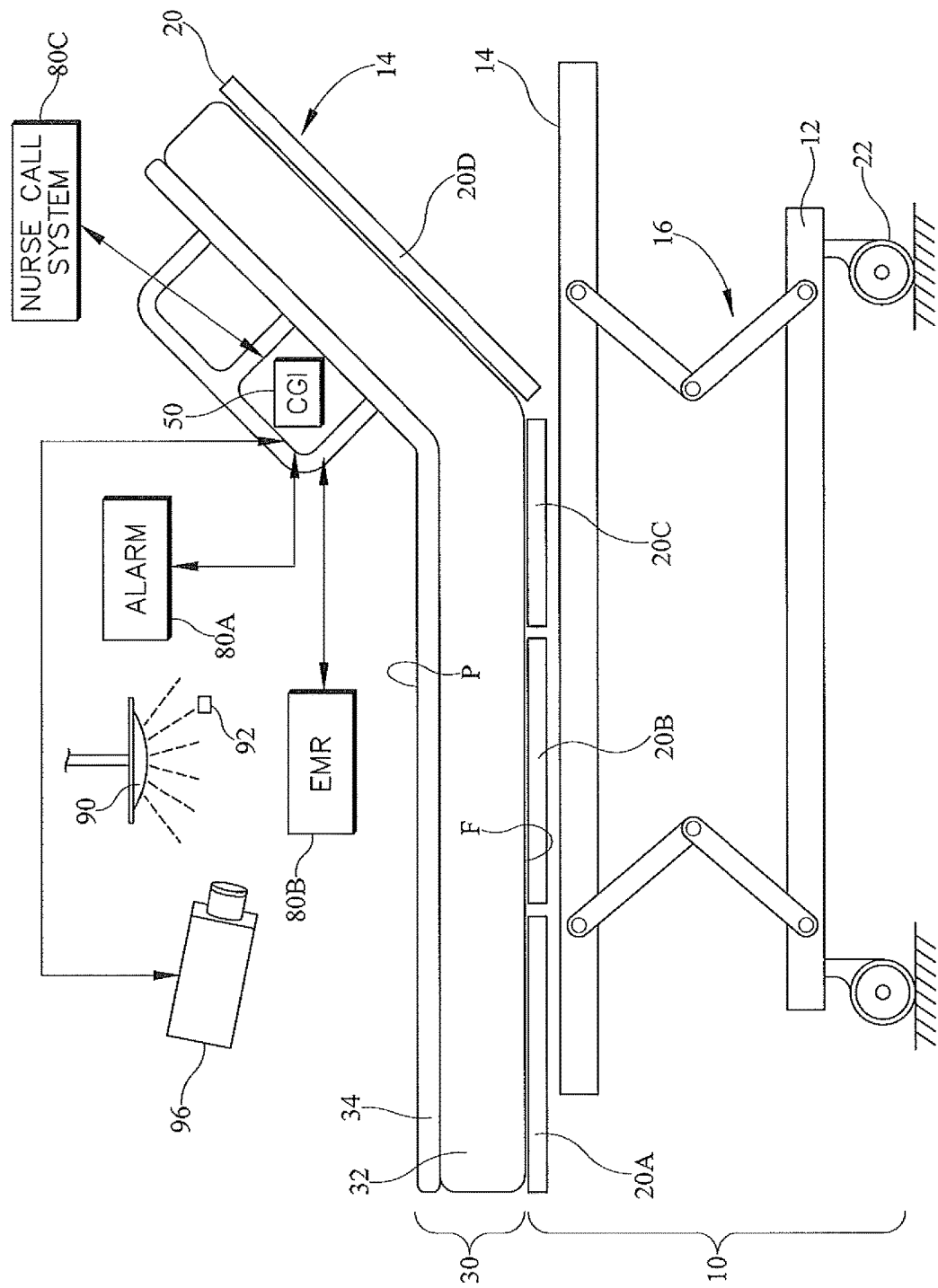
FIG. 1 is a diagram of a system for detecting skin abnormalities such as pressure ulcers and precursors to pressure ulcers in which an image capture device is used to carry out a method of detection.

FIG. 1 shows one embodiment of a system to detect pressure ulcers or precursors thereto. The pressure ulcer detection system is illustrated in the context of a hospital bed for a patient or occupant. The bed includes a person support apparatus or framework 10 comprising a lower frame 12 an upper or elevatable frame 14, and supports 16 which support the upper frame on the lower frame. The upper frame 14 includes a deck 20 comprised of individual deck sections 20A, 20B, 20C, 20D. Supports 16 and associated actuators (not illustrated) are configured to adjust the elevation of the upper frame 14 relative to the lower frame 12. A set of casters 22 extends from the lower frame to the floor.

A person support surface assembly 30 rests on the framework 10. The illustrated support surface assembly 30 includes a mattress 32 and a mattress topper 34 on top of the mattress. Alternatively the support surface assembly may include only mattress 32. The support surface assembly has a frame side F and a patient side P. The patient side is the side that faces and is in contact with the patient. If the support surface assembly includes a topper the patient side is the upper surface of the topper. If the support surface assembly includes only a mattress the patient side is the upper surface of the mattress. Collectively, framework 10 and person support surface assembly 30 may be referred to as a support system. In the foregoing and other examples of this specification the person support system is a bed. However in other embodiments the person support system may be a wheelchair, a stretcher, an operating room table, or any other apparatus configured to support a person thereon.

Figure 2:
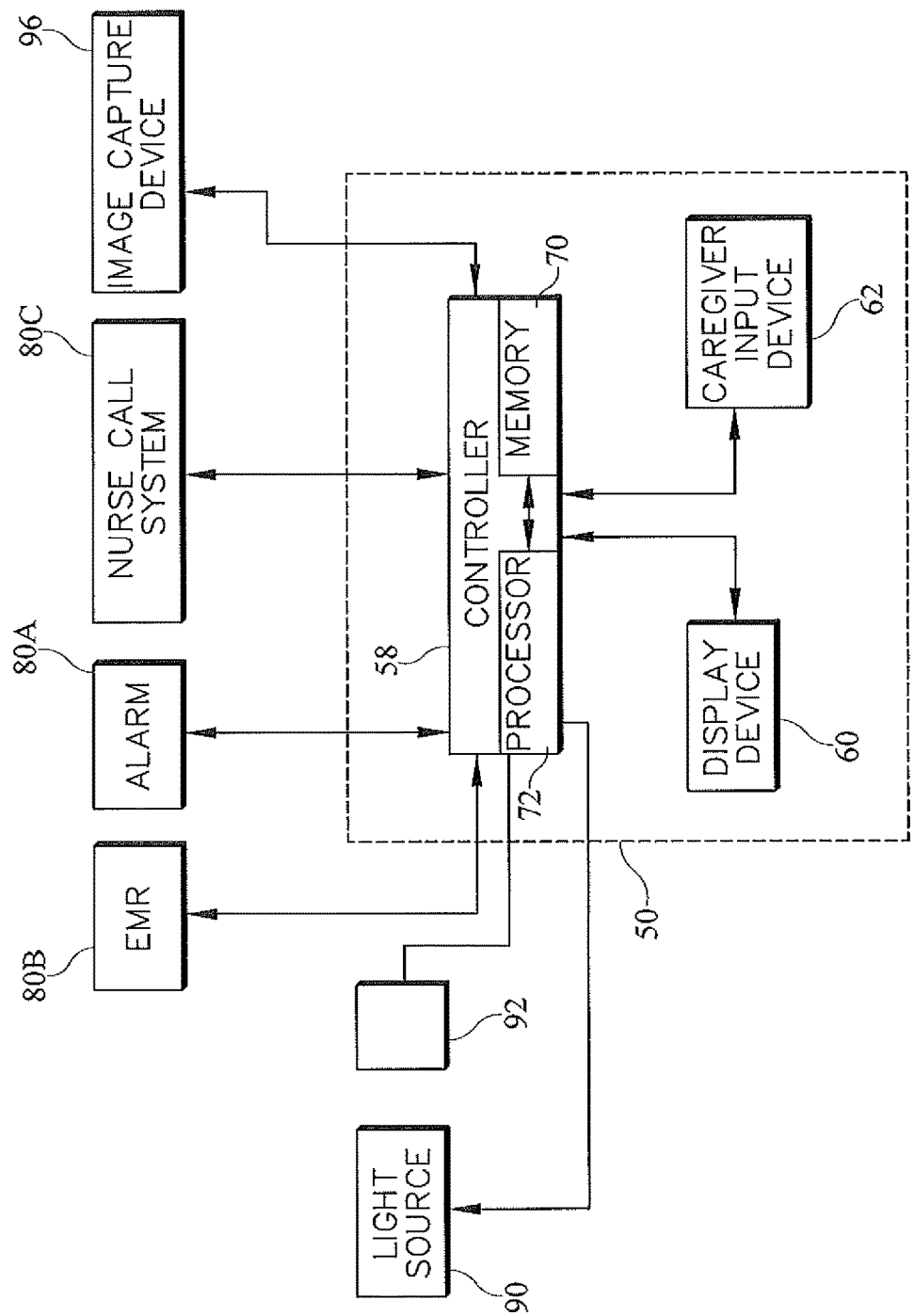
FIG. 2 is a block diagram showing selected elements of FIG. 1.

Referring additionally to FIG. 2, a caregiver interface 50, abbreviated as CGI in FIG. 1, includes a display device 60, for example a video monitor, and an input device 62, for example a keyboard. The illustrated caregiver interface includes a controller 58. The controller comprises a memory 70 to store information and a processor 72 to process information, for example by executing an algorithm which is stored in the memory and which produces a prediction of a pressure ulcer based on inputs to the algorithm. Other architectures are possible. For example the memory need not be an element of the controller. The controller, whether it includes the memory or not, need not be a component of the caregiver interface. The controller may be a controller dedicated to controlling the pressure ulcer detection system, or it may be a controller that is also configured to control at least one function of the framework 10 and/or the surface assembly 30 in addition to controlling the pressure ulcer detection system. One example of a function of the framework is a function that changes the elevation of upper frame 14 relative to lower frame 12. One example of a function of the support surface assembly is a function that pumps air into or vents air from an air bladder component of the support surface assembly. The display device 60 may be a display device dedicated to displaying information related to the pressure ulcer detection system, or it may be a display device that is also configured to display information related to at least one function of the framework 10 and/or the surface assembly 30. The input device 62 may be an input device dedicated to accepting inputs for the pressure ulcer detection system, or it may be an input device that is also configured to accept inputs related to at least one function of the framework 10 and/or the surface assembly 30. The controller 58 is configured to communicate with one or more information recipients or destinations 80 such as alarm 80A, an electronic medical record (EMR) system 80B, and a nurse call system 80C. The output of alarm 80A may be an audio output, a visual output, a tactile output, or some combination thereof.

FIGS. 1-2 also show a light source 90 dedicated to the pressure ulcer detection methods described herein and a light intensity sensor 92. The light source produces light in a portion of the spectrum that a light collector, described below, is sensitive to. A dedicated light source may not be necessary in all cases, for example if the ambient light available from windows and lighting fixtures is sufficient for carrying out the methods disclosed herein.

FIGS. 1-2 also show an image capture device 96 or collector. One example of such a device is a camera. The image capture device 96 is configured to capture or collect or detect electromagnetic radiation reflected from the patient. The collected radiation may be from any part of the electromagnetic spectrum determined to be suitable for the methods described herein. In this specification, "light" and "radiation" are used as a convenient shorthand to refer to electromagnetic radiation at any wavelength λ, even outside the visible portion of the electromagnetic spectrum. Similarly, "color" is used to refer to light/radiation at a specific wavelength or wavelengths even if the wavelengths are outside the visible portion of the electromagnetic spectrum. "Illuminate" and its variants mean causing the light/radiation to be incident on an object of interest. "Optical" and its variants are also not limited to the visible portion of the spectrum. One example of a collector is a camera designed to be sensitive to a particular wavelength band, e.g. visible light or infrared. The image capture device 96 is also configured to transmit data to controller 58 or to otherwise make information available to the controller.

The methods described below are concerned with optical properties exhibited by a target region or target site. In general a target region is a region of skin that a clinician wishes to evaluate for the presence of an abnormality or precursors to the abnormality. A target region of particular interest is a region of skin that is known or believed to be susceptible to the development of abnormalities such as pressure ulcers. As used herein, the phrase "region of skin" is used to identify an externally visible region or area of the patient's body. However it is known that the early warning signs of a pressure ulcer can occur beneath the externally visible surface of the stratum corneum. Hence, the phrases "region of skin", "target region", "target site" and their equivalents and analogues are not limited to an area of the skin surface, but also include tissue beneath that area that can exhibit signs of a pressure ulcer or its precursors. Other methods described below are concerned with the optical properties exhibited by a target region in comparison to the optical properties exhibited by a reference region of the skin. A reference site or region or a reference tissue sample is a site or sample chosen because the tissue is known or believed to be healthy. The phrase "reference region", like "target region", includes tissue beneath the skin surface. In the case of both the target region and the reference region, the optical properties include light intensity and spectral content.

During operation, the image capture device collects light reflected from the patient occupying the bed. Processor 72 receives data from image capture device 96. The processor processes that information to assess the properties of the reflected light relative to the properties of the incident light. The outcome of the assessment is communicated to a destination. A variety of methods which can be carried out by the apparatus are described below.

Method/Algorithm 1:

In one method of operation the possibility of pressure ulcer development is based on the intensity of light reflected from a target region (also referred to as a target site) relative to the intensity of light incident on the target region at essentially the same time. Unless otherwise noted, the explanations in this specification do not, as a rule, consider losses that might occur as the light propagates from its source to the target region or, in the case of reflected light, from the target region back to a detector. To the extent such losses are present and meaningful they can be easily accounted for. The tissue at the target site is referred to herein as target tissue or a target tissue sample. Intensity of the light is the energy per unit time per unit area, i.e. power flux). Referring additionally to the block diagram of FIG. 3, the method illuminates the target site (block 110). The illumination may be an active step such as turning on a suitable light such as light 90, or it may be a passive step such as relying on available ambient light. The intensity $I_{INCI}$ of the incident light is known from a prior calibration of the light source or by measuring the light intensity with sensor 92. The camera 96 is a collector which collects the light reflected from the target as indicated at block 120. In the illustrated configuration the camera itself is configured to measure the intensity of the reflected light $I_{REFL}$ and to make the outcome of the measurement available to processor 72. At block 130 processor 72 carries out an evaluation. The evaluation is an assessment (sub-block 132) of the relative intensities of the incident and reflected light to determine if a meaningful dissimilarity exists between the two intensities. The presence or absence of a meaningful dissimilarity can be assessed by any suitable method. Suitable methods include calculating the arithmetic difference between the two intensities (e.g. $I_{INCI}-I_{REFL}$) and calculating the ratio of the intensities (e.g. $I_{INCI}/I_{REFL}$). (Throughout this specification an arithmetic difference in light intensities (or other properties) may be used as an example of a dissimilarity in intensities (or other properties) without intent to limit the meaning of "dissimilarity" to an arithmetic difference or to limit the optical property under consideration to intensity.) If the dissimilarity is represented as a calculated value, such as the difference or ratio of intensities, the calculated value can be considered to be a "score" which quantifies the dissimilarity.

At block 140 the outcome of the assessment is communicated to or otherwise made available to a destination 80. In one mode of operation the communication occurs (or the information is made available) irrespective of whether the assessment is favorable (no abnormality) or unfavorable (presence or possible presence of an abnormality). In another mode of operation the communication occurs (or the information is made available) only if the assessment is unfavorable. In the latter case the absence of a communication can be thought of as a null communication.

The content of the communication may depend on the nature of the destination. For example if the destination is alarm 80A, the communication may be a signal which causes activation of the alarm. If the destination is nurse call system 80C the communication may be a signal that turns on an alert light at a nurse station, displays patient related information on a monitor at the nurse station and turns on a light outside the patient room. If the destination is EMR 80B the communication may include patient related data. Patient related data may include information related to the detection or prediction of a pressure ulcer (such as its location and estimated severity) as well as patient physiological information.

Figure 3:
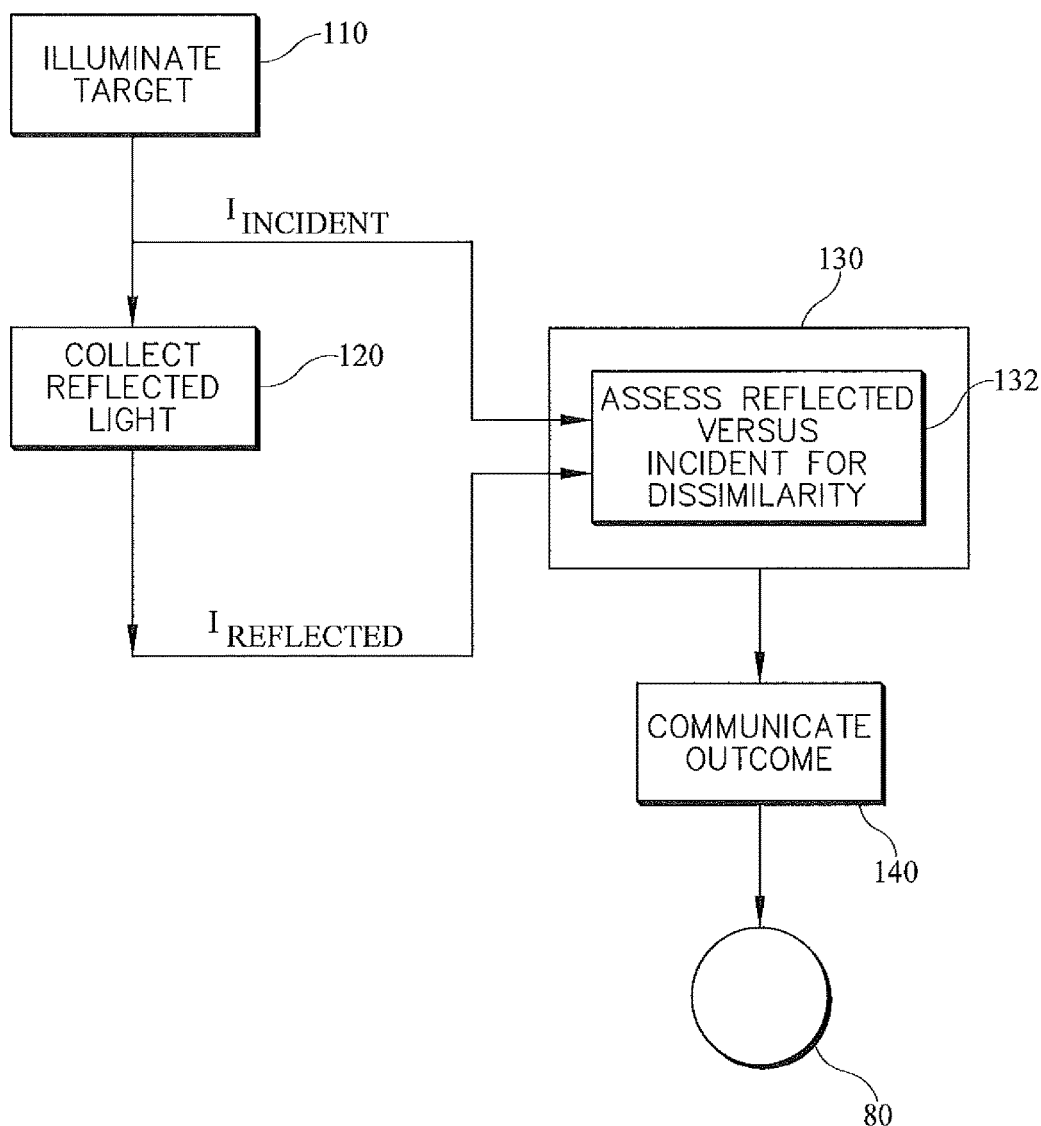
FIG. 3 is a block diagram showing a method (method 1) for detecting skin abnormalities such as pressure ulcers or precursors to pressure ulcers, the method involving an assessment of the relative intensity of light used to illuminate a target site and light reflected from the target site at substantially the same time.
Figure 4:
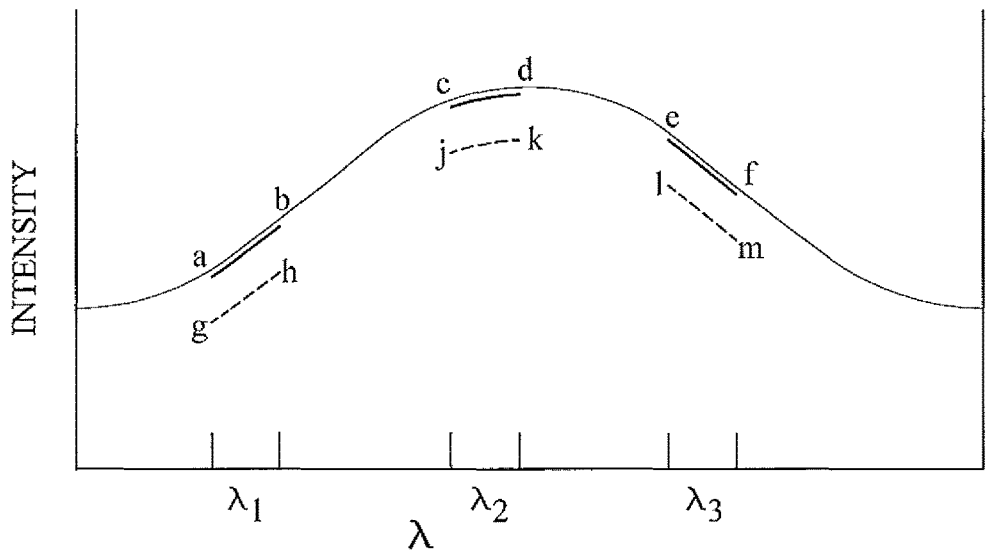
FIG. 4 is a graph illustrating one option for carrying out method 1, the option including illuminating the target site with light of one or more discrete wavelengths and carrying out the assessment at the same one or more wavelengths.

Table 1 below and FIG. 4 describe certain options involving the spectral content of the incident light and the spectral band or bands of the reflected light used in the assessment at sub-block 132 of FIG. 3.

TABLE 1

| Option | Spectrum of Incident Light | Evaluation/Assessment |
|---|---|---|
| 1 | Narrow (at least one of λ$_1$ through λ$_n$) | Narrow (subset of incident λ's) |
| 2 | Broad | Narrow (One or more λ's of interest within the broader spectrum of the incident light) |
| 3 | Broad (B1) | Broad (B2) |

In option 1 (FIG. 4) the incident light is narrow spectrum light. A narrow spectral band is a wavelength band whose width is no more than about 20 nanometers, or about 10 nanometers on either side of a center wavelength. Unless otherwise noted or otherwise clear from the context, wavelengths specified in this specification are center wavelengths, which may also be referred to as discrete wavelengths. As seen from the table, the illumination is carried out at one or more wavelengths $\lambda_i$. The assessment of block 132 is carried out for a subset of those wavelengths. As used herein, "subset" refers to both proper subsets (a subset that includes fewer than all the elements of the set) and improper subsets (a subset which is identical to the set), but does not include the null set (no elements). In the example of FIG. 4 the light solid line shows a broad continuous spectrum for reference only. The illumination is carried out at $\lambda_1$, $\lambda_2$, and $\lambda_3$, (heavy solid line segments). The assessment is carried out for the same three wavelengths. The dashed line segments show the reflected light intensity at each of those wavelengths. The assessment identifies dissimilarities such as the intensity from a to b, relative to the intensity from g to h, the intensity from c to d, relative to the intensity from j to k, and the intensity from e to f, relative to the intensity from l to m.

Figure 5:
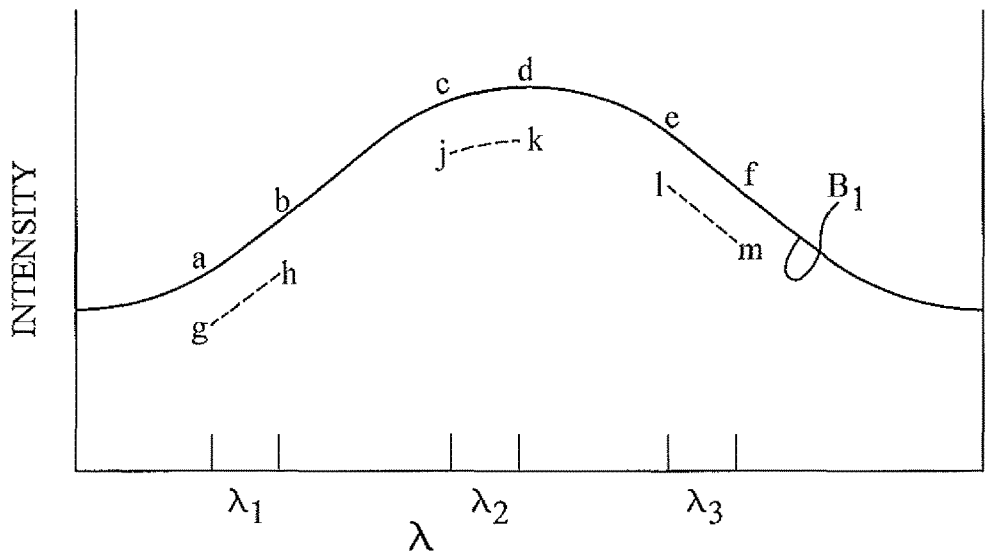
FIG. 5 is a graph similar to that of FIG. 4 showing a second option including illuminating the target site with broadband light and carrying out the assessment at one or more discrete wavelengths.

In option 2 (FIG. 5) the incident light is broad spectrum light B1. In the example of FIG. 5 the intensity of the incident light is shown by the solid line. Broad spectrum light has a wavelength band broader than narrow spectrum light but may nevertheless be bounded by upper and/or lower wavelength limits. The assessment of block 132 is carried out for discrete wavelengths of interest within the broader spectrum. The intensity of the reflected light is shown by the dashed line segments. In the example of FIG. 5 the illumination is carried out across a broad spectrum however the assessment of relative intensity is carried out only at $\lambda_1$, $\lambda_2$, and $\lambda_3$.

Figure 6:
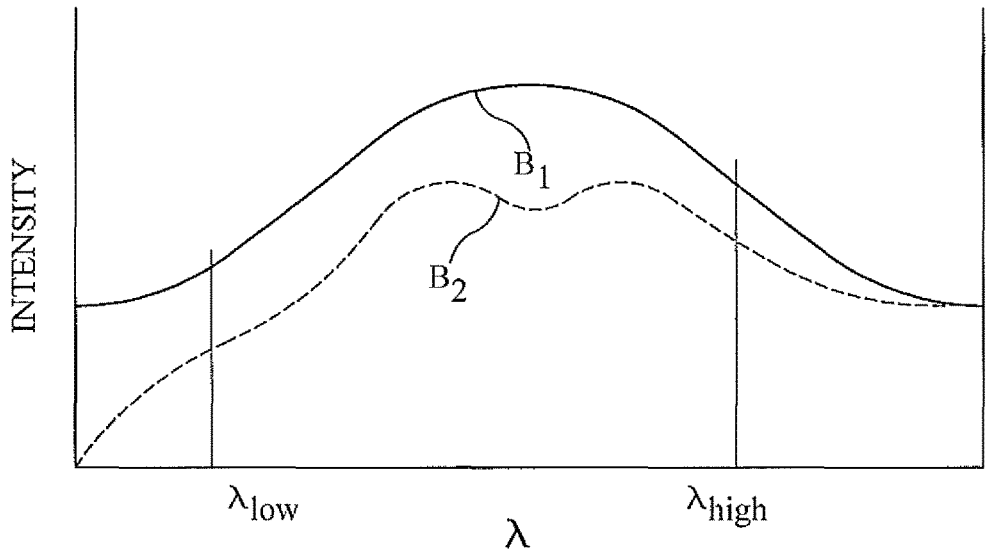
FIG. 6 is a graph similar to that of FIGS. 4 and 5 showing a third option including illuminating the target site with broadband light and carrying out a broadband assessment.

In option 3 (FIG. 6) the incident light is broad spectrum light B1. The assessment of block 132 is carried out for a broad spectrum B2 which is not necessarily as broad as B1. In the example of FIG. 6 the intensity of the incident light is shown by the solid line. The intensity of the reflected light is shown by the dashed line. The assessment of relative intensity is carried out across the sub-spectrum extending from $\lambda_{LOW}$ to $\lambda_{HIGH}$.

Figure 7:
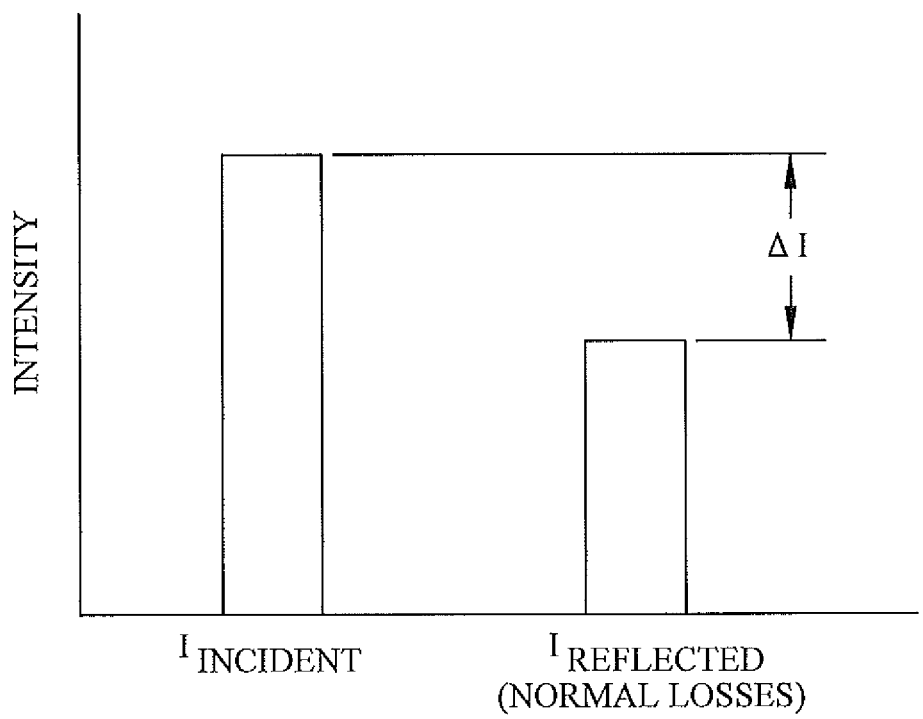
FIG. 7 is a bar graph illustrating the principal of disregarding any component or portion of a detected dissimilarity between light incident on a patient's skin and light reflected from a patient's skin if that component or portion of the dissimilarity would be expected to occur even if the skin were normal.

Whether the assessment is based on broadband light or narrow band light, the assessment may disregard any component or portion of a detected dissimilarity that would be expected to occur if the skin were normal. For example light scattering could cause such a dissimilarity. In other words the dissimilarity would be considered meaningful only if it exceeds some threshold which accounts for normal losses as the light propagates from its source to the skin and then back to the light collector. FIG. 7 shows an example in which the intensity of the light incident on a healthy skin sample and the intensity of the light reflected from that sample differ by $\Delta I$ due to nothing more than losses. Therefore a dissimilarity, such as a difference in intensity would be considered meaningful only if it were greater than $\Delta I$.

The technique described above can be used on multiple target sites, each considered individually.

One useful wavelength $\lambda$ is about 415 nm which is the wavelength corresponding to peak absorption of radiation by oxygenated hemoglobin, Hgb. In other words tissue rich in Hgb will absorb much of the 415 nm incident radiation ($I_{INCI,415}$) and therefore reflect relatively little radiation at 415 nm ($I_{REFL,415}$). The arithmetic difference $I_{INCI,415}-I_{REFL,415}$ and the quotient $I_{INCI,415}/I_{REFL,415}$ will therefore be large.

Another useful wavelength is about 435 nm which is the wavelength corresponding to peak absorption of radiation by deoxygenated hemoglobin, deoxy-HB. In other words tissue rich in deoxy-HB will absorb much of the 435 nm incident radiation ($I_{INCI,435}$) and will therefore reflect relatively little radiation at 435 nm ($I_{REFL,435}$).

Another useful wavelength is about 335 nm which is the wavelength corresponding to peak absorption of melanin. In other words tissue rich in melanin will absorb much of the 335 nm incident radiation ($I_{INCI,335}$) and therefore reflect relatively little radiation at 335 nm ($I_{REFL,335}$).

Another useful wavelength is 955 nm which is the wavelength at which liquid phase water is highly reflective. In other words water in its liquid phase will reflect much of the 955 nm incident radiation. That is, $I_{INCI,955}$ is approximately equal to $I_{REFL,955}$. Subepidermal water accumulation, such as accumulation between the epidermis and the dermis, or accumulation in the upper portion of the dermis, can be a sign of tissue damage. Therefore high intensity of reflection at 955 nm ($I_{REFL,955}$) indicates the presence of water, therefore tissue damage, whereas low intensity of reflection at 955 nm indicates the absence of water, therefore healthy tissue.

Each of the foregoing examples considers only one wavelength. Multiple wavelengths can also be considered. For example, low values of both Hgb and Deoxy-HB (as indicated by observing the intensity of reflected light relative to that of the incident light at both 415 and 435 nm ($I_{INCI}/I_{REFL}$ and $I_{INCI}/I_{REFL}$) can indicate abnormally low blood flow rate (volume or mass per unit time) or the absence of blood flow.

Another useful measure of tissue health is the ratio of Hgb to Deoxy-HB at the target site as indicated by the ratio $I_{REFL,415}/I_{REFL,435}$. Lower values of the intensity ratio can indicate either a deficit of oxygenated hemoglobin or can indicate local pooling of deoxygenated hemoglobin.

Figure 8:
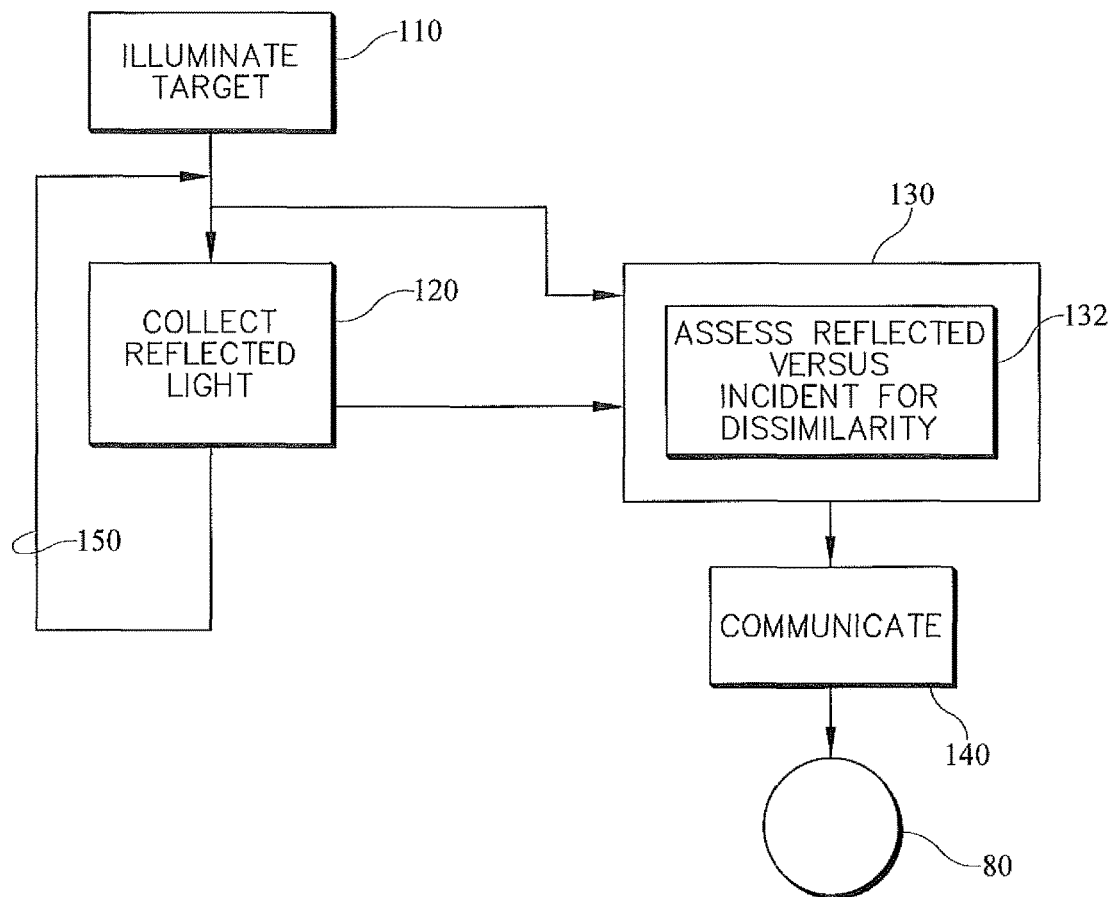
FIG. 8 is a block diagram showing a method (method 2) for detecting skin abnormalities such as pressure ulcers or precursors to pressure ulcers, the method involving an assessment of the relative intensity over time of light used to illuminate a target site and light reflected from the target site.
Figure 9:
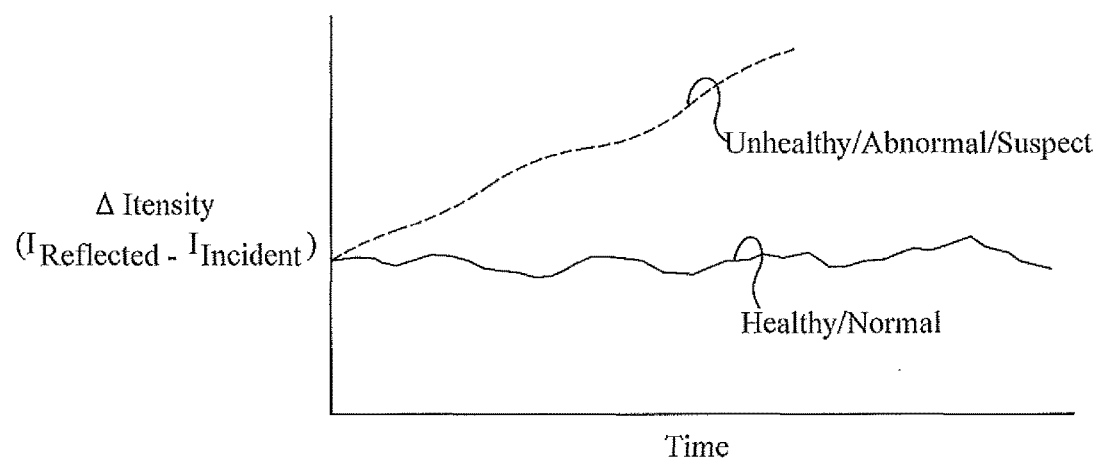
FIG. 9 is a graph illustrating how a substantially constant dissimilarity, exemplified as a light intensity difference (solid line), indicates healthy or normal tissue, or at least a dissimilarity that does not change over time, even though the difference may be high enough to be consistent with the presence of a pressure ulcer and also illustrating how a change in the intensity difference (broken line) indicates an abnormality such as a pressure ulcer, or at least a region of skin that is suspect.

Method/Algorithm 2:

Method 1, described above, may yield a false positive if the target region happens to exhibit a dissimilarity in reflected versus incident light intensity which, while consistent with the dissimilarity expected if a pressure ulcer were present, is actually the result of some other condition. Referring to FIGS. 8-9 method 2 addresses this possibility by monitoring the dissimilarity over time. Method 2 is based on how the intensity of light reflected from the target region changes over time in relation to the intensity of light incident on the target region. The block diagram of FIG. 8 is the same as that of FIG. 3 with the addition of a loop 150. The loop causes collection step 120 and assessment step 132 to be repeated at discrete times, e.g. once every 30 minutes, or to be repeated substantially continuously. A substantially constant dissimilarity, exemplified as an intensity difference (FIG. 9, solid line) indicates healthy or normal tissue, or at least a dissimilarity that does not change over time, even though the difference may be high enough to be consistent with the presence of a pressure ulcer. A change in the intensity difference (FIG. 9, broken line) indicates an abnormality such as a pressure ulcer, or at least a region of skin that is suspect. As with method 1, method 2 may disregard any component or portion of a detected dissimilarity that would be expected to occur if the method were applied to normal skin. Method 2 may also disregard temporal differences that are attributable to causes other than development of a pressure ulcer. For example the skin of a dehydrated person who is being re-hydrated may exhibit some temporal change in the intensity of reflected light relative to that of incident light as a result of the hydration. In other words the change of intensity over time is considered meaningful only if it exceeds some threshold above and beyond what would be expected as a result or rehydration.

Method/Algorithm 3:

Another useful measure of tissue health is a relationship between the intensity of radiation reflected by a target tissue sample at one or more wavelengths and the intensity of radiation reflected by a reference tissue sample (also referred to as simply reference tissue) at the same one or more wavelengths. The target tissue sample is from a target site. The target site is a site chosen to be evaluated for tissue damage. The reference tissue sample is from a reference site, also referred to as a reference region.

Figure 10:
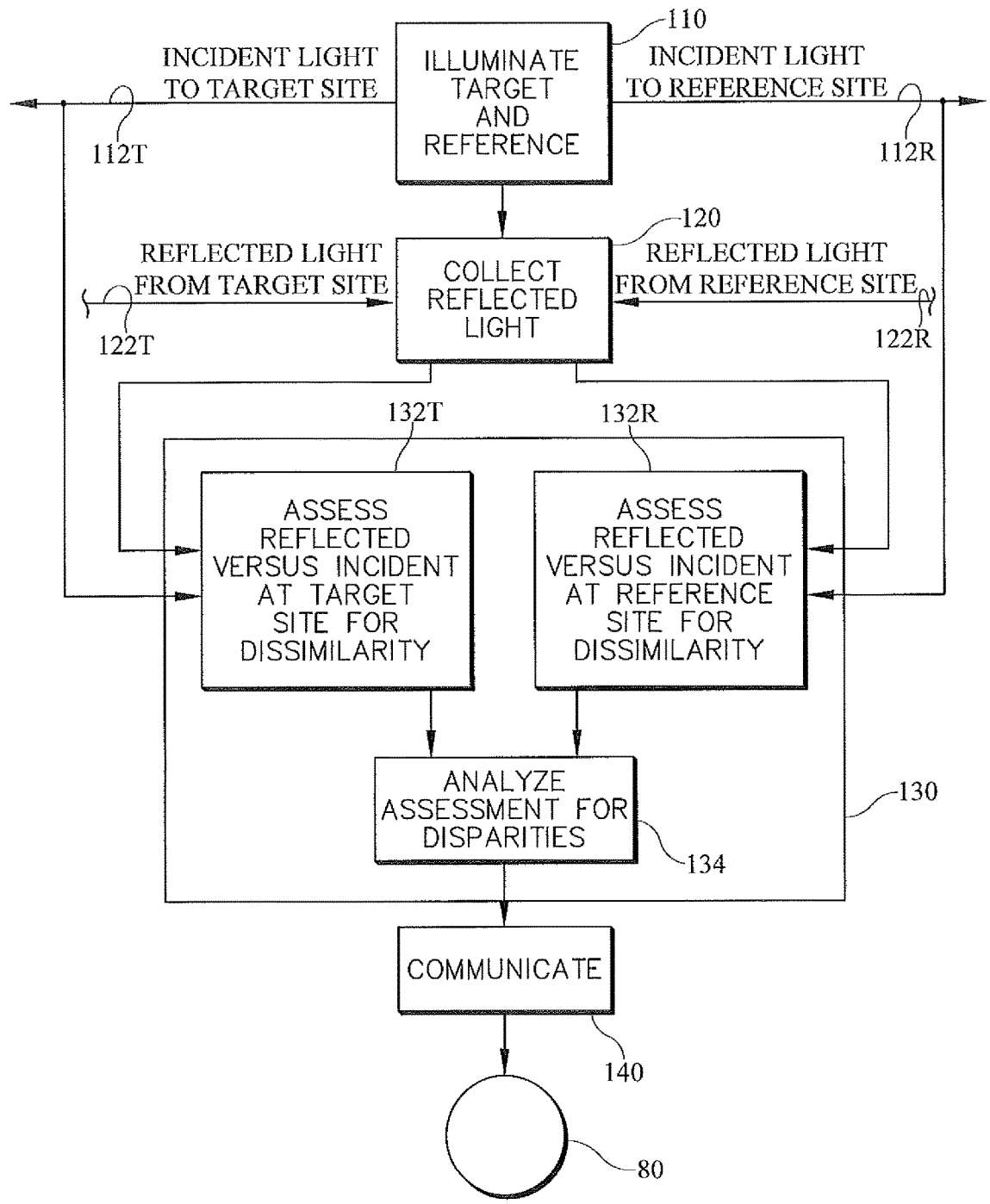
FIG. 10 is a block diagram showing a method (method 3) for detecting skin abnormalities such as pressure ulcers or precursors to pressure ulcers, the method involving an assessment of the relative intensity of light reflected from a target site and light reflected from a reference site at substantially the same time.

Referring to FIG. 10 method 3 illuminates the target site and the reference site (block 110, branches 112T, 112R). A collector such as camera 96 of FIG. 1 collects the light reflected from the target and reference sites (block 120, branches 122T, 122R). At block 130 processor 72 carries out an evaluation. Unlike methods 1 and 2, evaluation 130 of method 3 includes individual assessment sub-blocks 132T, 132R and an analysis sub-block 134. At sub-block 132T the algorithm assesses the intensity of reflected light relative to the intensity of incident light at the target site. At sub-block 132R the algorithm assesses the intensity of reflected light relative to the intensity of incident light at the reference site. At sub-block 134 the method performs an analysis to uncover meaningful disparities between any dissimilarities identified at blocks 132T, 132R. As used herein the term "disparity" is analogous to "dissimilarity" but is used when the subject of the evaluation is a dissimilarity in light intensity whereas "dissimilarity" is used when the subject of the evaluation is the light intensities themselves. Determining the presence or absence of a meaningful disparity can be carried out by any suitable method. Suitable methods include calculating the arithmetic difference between two intensity differences (e.g. $(I_{INCI}-I_{REFL})_{TARGET}-(I_{INCI}-I_{REFL})_{REFERENCE}$). At block 140 the outcome of the assessment is communicated to or otherwise made available to a destination 80.

Method 3 is similar to method 1 in that both methods assess one or more light properties at substantially a fixed point in time. Method 3 differs from method 1 in that method 3 considers the intensity of reflected light at both a target site and a reference site (accounting, if necessary, for any differences in intensity between the light incident at those sites and the intensity of the light emitted at the source or sources of the light) whereas method 1 considers the properties of incident and reflected light at only a target site.

Figure 11:
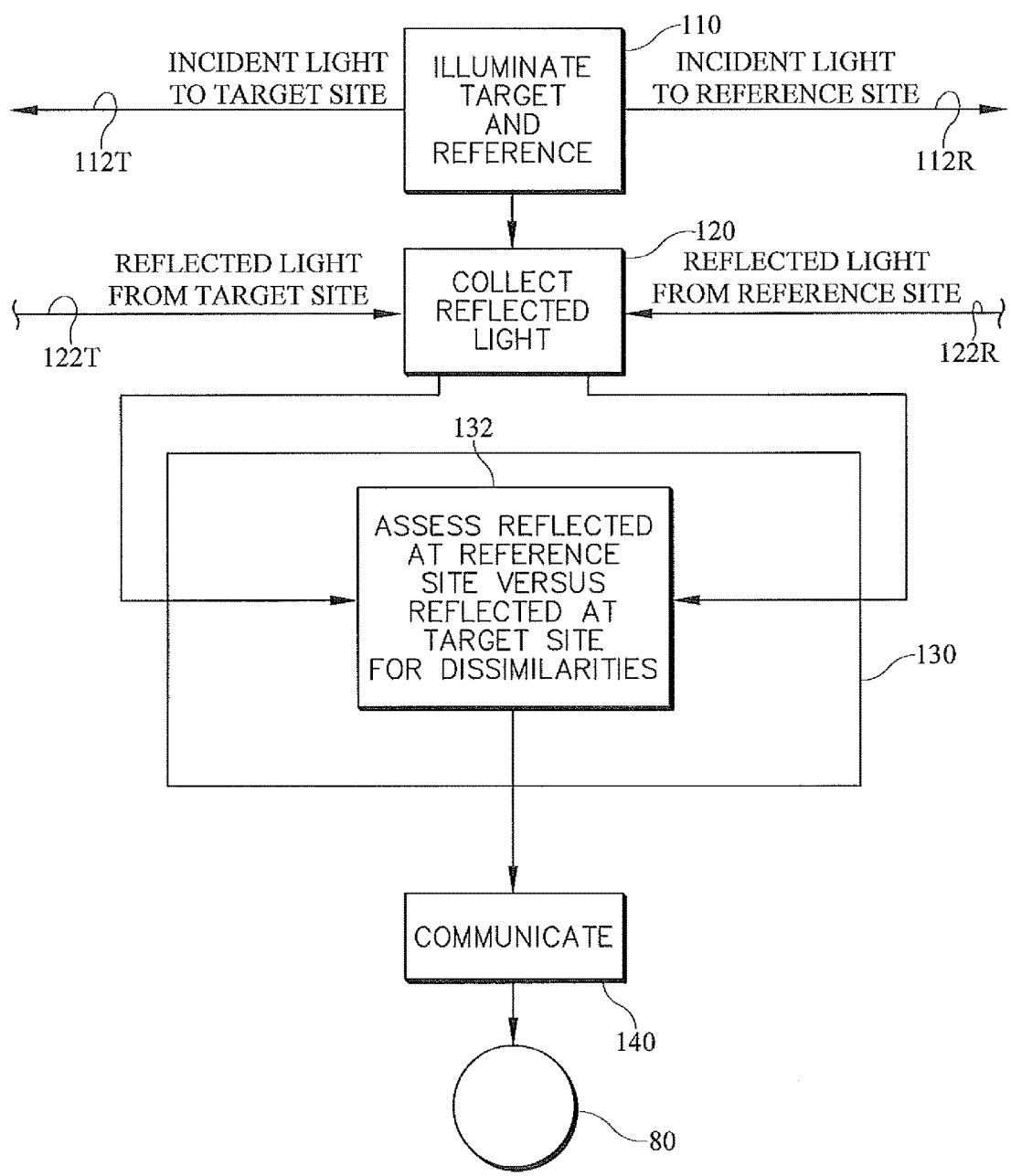
FIG. 11 is a block diagram showing a simplified version of the method of FIG. 10.

FIG. 11 shows a simplified variant of method 3. The simplified variant is suitable if the target site and the reference site are analogous sites, also referred to as sister sites. In this context, sister sites are those that reflect light with about the same intensity (for a given intensity of incident light) when the tissue at those sites is in a normal or healthy state. In that case separate assessment steps (132T, 132R of FIG. 10) and analysis step 134 can be replaced with a single step evaluation 130 involving nothing more than assessing dissimilarities (sub-block 132) between the intensity of light reflected from the reference site relative to the intensity of light reflected from the target site.

Under certain conditions the simplified variant of FIG. 11 may also be applicable even if the reference site and the target site are nonanalogous, i.e. they reflect light with different intensities (for a given intensity of incident light) when the tissue at those sites is in a normal or healthy state. This is because, provided the dissimilarity (e.g. the difference in reflected intensities) is known and repeatable, it can be accounted for. This can be done at block 130 by, for example, disregarding any dissimilarity between the reflected intensities which is consistent with the known dissimilarities attributable to the use of nonanalogous sites.

Table 2 shows, in a largely non-quantitative manner, the conclusions arising from high intensity and low intensity reflections of 415 nm radiation from the target and reference sites. Because Hgb absorbs 415 nm radiation, a strong or high intensity reflection reveals low levels of Hgb whereas a weak or low intensity reflection reveals high levels of Hgb. The ratio of the intensities at the target and reference sites is $(I_{TGT}/I_{REF})_{REFL,415}$. Ratios significantly greater than 1.0 indicate that the target tissue is unhealthy or is at least suspect or at risk. For economy of expression, throughout this specification the term "unhealthy" includes tissue which may not have deteriorated to a state of definite unhealthiness, but nevertheless exhibits a sign of being at risk of deterioration to a state of unhealthiness or exhibits a sign which causes suspicion about it's present or future state of health. Conversely, "healthy" means not unhealthy according to the preceeding definition of "unhealthy". A ratio of about 1.0 indicates that the target tissue is healthy.

TABLE 2

Reflection Intensity and Ratios at 415 nm

| | Target Site | | Reference Site | | Score: | |
|---|---|---|---|---|---|---|
| λ | $I_{TGT}$ | Hgb | $I_{REF}$ | Hgb | $I_{TGT}/I_{REF}$ | Conclusion |
| 415 nm | HIGH | low (bad) | LOW | high (good) | >>1.0 | UN-HEALTHY |
| | LOW | high (good) | LOW | high (good) | ≈1.0 | HEALTHY |
| | HIGH | low (bad) | HIGH | low (bad) | | Not considered. Reference site is known or presumed to be healthy |
| | LOW | high (good) | HIGH | low (bad) | | |

Table 3 shows, in a largely non-quantitative manner, the conclusions arising from high intensity and low intensity reflections of 435 nm radiation from the target and reference sites. Because deoxy-HB absorbs 435 nm radiation, a strong or high intensity reflection reveals low levels of deoxy-HB (high levels of oxygenation) whereas a weak or low intensity reflection reveals high levels of deoxy-HB (low levels of oxygenation). The ratio of the intensities at the target and reference sites is $(I_{TGT}/I_{REF})_{REFL,435}$. Ratios significantly less than 1.0, which correspond to ratios of $(I_{REF}/I_{TGT})_{REFL,435}$ significantly greater than 1.0, indicate that the target tissue is unhealthy. Ratios of $(I_{TGT}/I_{REF})_{REFL,435}$ or $(I_{REF}/I_{TGT})_{REFL,435}$ approximately equal to 1.0 indicate that the target tissue is unhealthy.

TABLE 3

Reflection Intensity and Ratios at 435 nm

| | Target Site | | Reference Site | | Score: | |
|---|---|---|---|---|---|---|
| λ | $I_{TGT}$ | DEOXY-hb | $I_{REF}$ | DEOXY-hb | $I_{REF}/I_{TGT}$ | Conclusion |
| 435 nm | HIGH | low (good) | LOW | high (bad) | | Not considered. Reference site is known or presumed to be healthy |
| | LOW | high (bad) | LOW | high (bad) | | |
| | HIGH | low (good) | HIGH | low (good) | ≈1.0 | HEALTHY |
| | LOW | high (bad) | HIGH | low (good) | >>1.0 | UN-HEALTHY |

Figure 12:
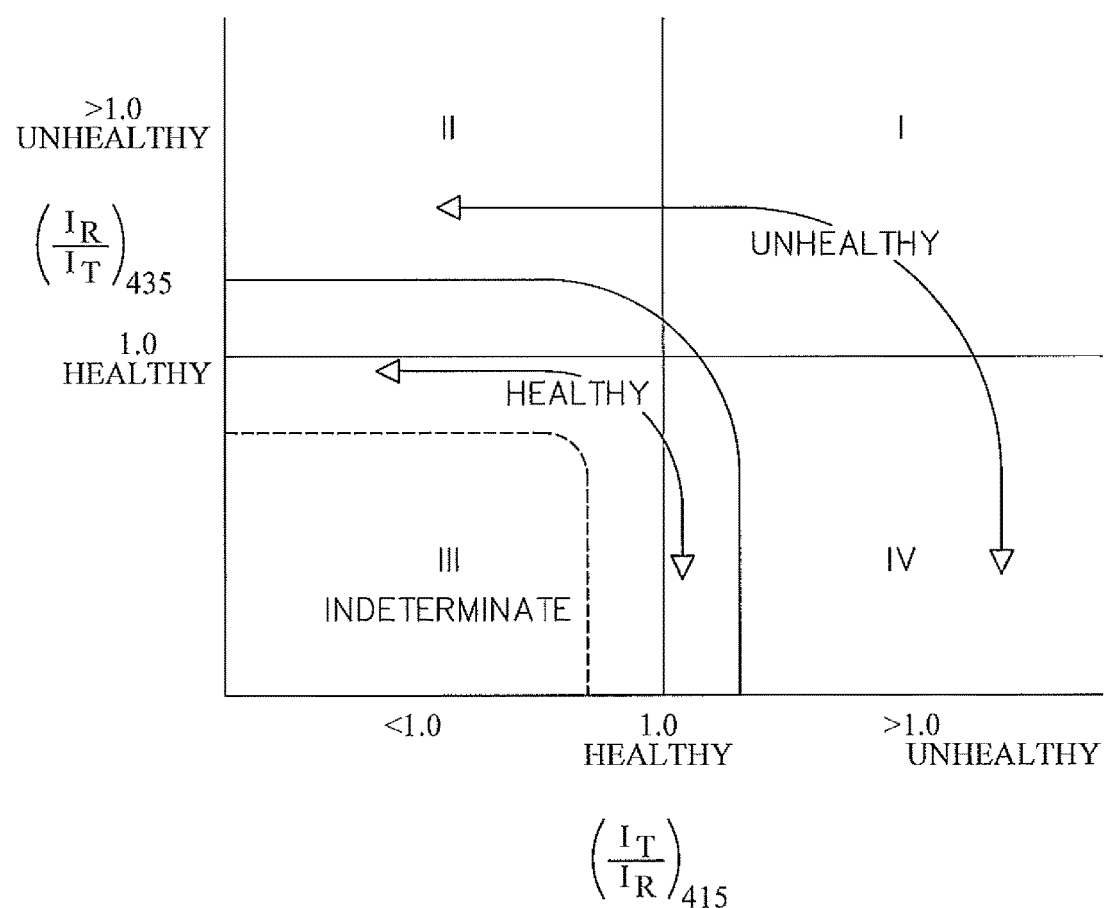
FIG. 12 is a graph of reflected light intensity ratio at 435 nm versus reflected light intensity ratio at 415 nm in which different regions of the graph correspond to healthy tissue, unhealthy tissue or tissue of indeterminate health.

FIG. 12 shows the results of tables 2 and 3 in a graph of $(I_{REF}/I_{TGT})_{REFL,435}$ versus $(I_{TGT}/I_{REF})_{REFL,415}$. The region above the solid line and to the right of the solid line corresponds to unhealthy tissue. The region between the solid line and the dashed line corresponds to healthy tissue. The region below the dashed line and to the left of the dashed line corresponds to tissue whose condition is indeterminate without additional information. The graph of FIG. 12 can be divided into four quadrants I, II, III, IV defined by the lines:

$(I_{REF}/I_{TGT})_{REFL,435}=1.0$; and $(I_{TGT}/I_{REF})_{REFL,415}=1.0$.

The dashed boundary is confined to quadrant III. The solid boundary has a first segment residing in quadrant II, a second segment residing in quadrant IV and a connecting segment residing in the lower left region of quadrant I. The solid and dashed boundaries define a band of healthy tissue. Alternatively the solid and dashed boundaries can be thought of as distinguishing a band of health tissue from unhealthy tissue and from tissue whose health is indeterminate without additional information.

When computing scores such as $I_{TGT}/I_{REF}$ or $I_{REF}/I_{TGT}$ it may be useful to subtract a melanin score because the presence of melanin will introduce a bias into the measured intensities of the reflections. Because that bias is not related to (i.e. is independent of) factors such as Hgb concentration at 415 nm and deoxy-HB concentration at 435 nm, the melanin represents noise that obscures the desired signal (the intensity of reflection as affected by Hgb and deoxy-HB). The ratios $I_{TGT}/I_{REF}$ and $I_{REF}/I_{TGT}$ in the foregoing discussion would therefore be replaced by $(I_{TGT}-I_{MEL})/(I_{REF}-I_{MEL})$ and $(I_{REF}-I_{MEL})/(I_{TGT}-I_{MEL})$ where $I_{MEL}$ is the intensity of radiation reflected by the melanin. The magnitude $I_{MEL}$ can be determined from a healthy tissue site by illuminating a healthy tissue site with radiation at one or more test wavelengths and observing the amount of radiation reflected. The test wavelengths are chosen to be wavelengths at which the absorption and reflection properties of the tissue are not expected to be affected by things other than melanin.

Figure 13:
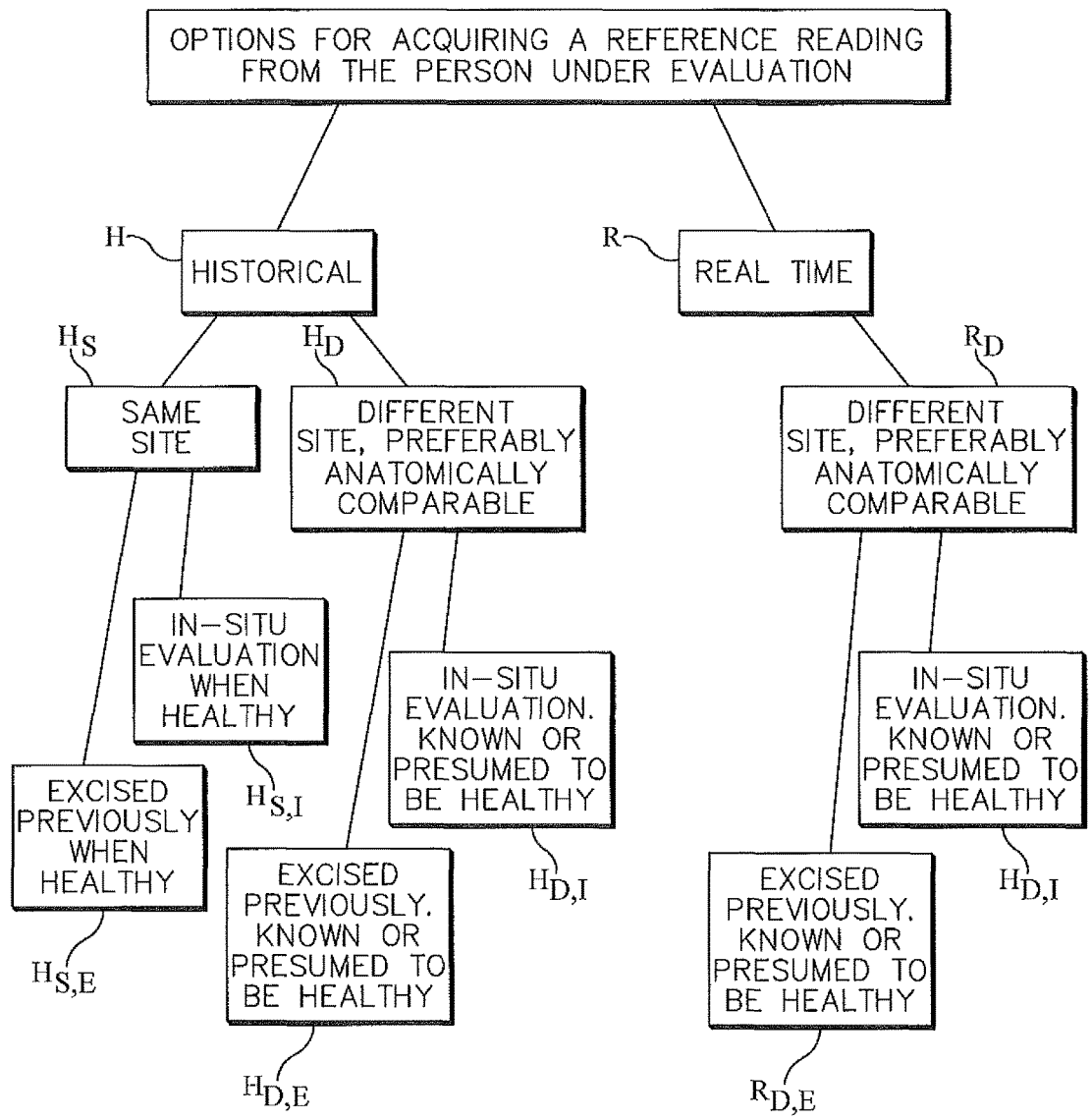
FIGS. 13 and 14 are charts showing options relating to suitable sources of a reference skin sample or a suitable reference site if the reference sample or site is from the person under evaluation.
Figure 14:
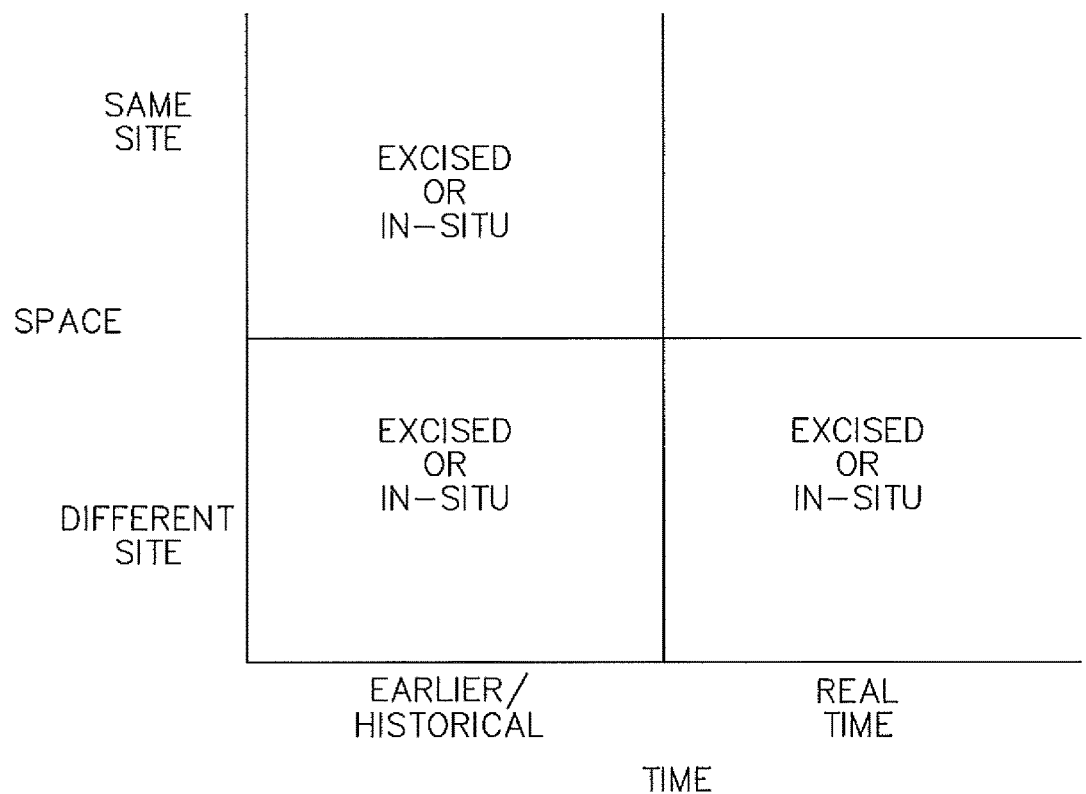

FIG. 13 is a diagram showing a number of options relating to the reference sample or reference site if the reference sample is from the person under evaluation. FIG. 14 is a diagram showing the same options on a spatial/temporal grid. The reference site may be a historical reference site, i.e. a site that had been previously evaluated when the tissue at the sight was known or believed to be healthy, with the results of the evaluation having been set aside for future use (node H). The historical reference site may be the same site as the site to be evaluated (node $H_S$) or may be a different site (node $H_D$). If the site is a different site it is preferably a sister site. A sister site is one whose tissue is known or believed to be healthy and whose tissue is believed to be a reasonably accurate surrogate for healthy tissue at the target site. Sister sites are described in more detail below. Irrespective of whether the reference site is the same as the site currently under evaluation ($H_S$) or a different site ($H_D$), the reference sample can be excised from the reference site and then evaluated (nodes $H_{SE}$, $H_{DE}$) or can be subject to in-situ evaluation (nodes $H_{SI}$, $H_{DI}$).

Alternatively the reference site may be a site evaluated in real time, i.e. evaluated at essentially the same time as the target sample is being evaluated (node R). In real time the site under evaluation could not serve as a reference site. Accordingly, the reference site is a different site, preferably a sister site (node $R_D$). The reference sample can be excised from the reference site (node $R_{DE}$) and then evaluated or can be subject to in-situ evaluation (node $R_{DI}$).

Figure 15:
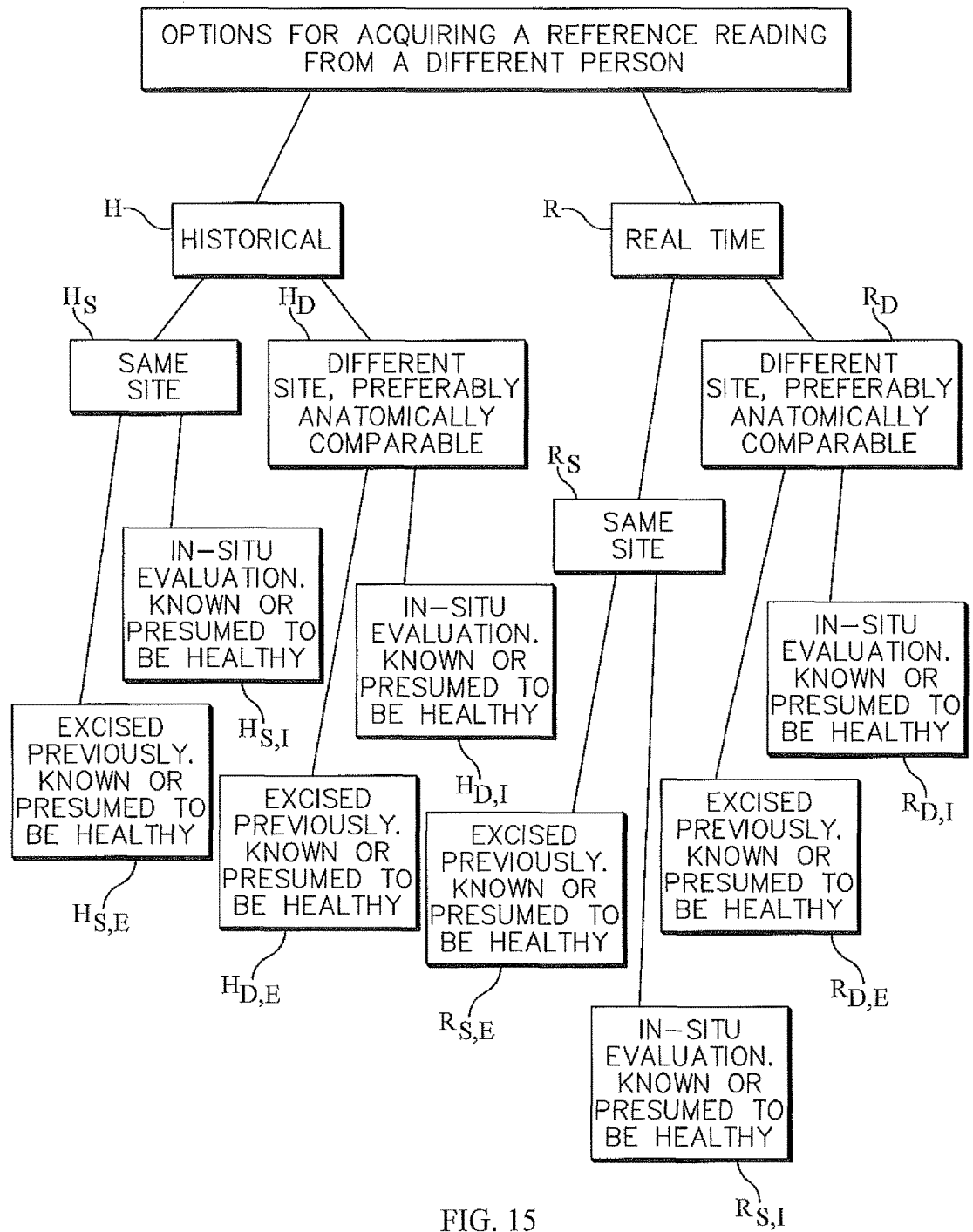
FIGS. 15 and 16 are charts showing options relating to suitable sources of a reference skin sample or a suitable reference site if the reference sample or site is from a person other than the person under evaluation.
Figure 16:
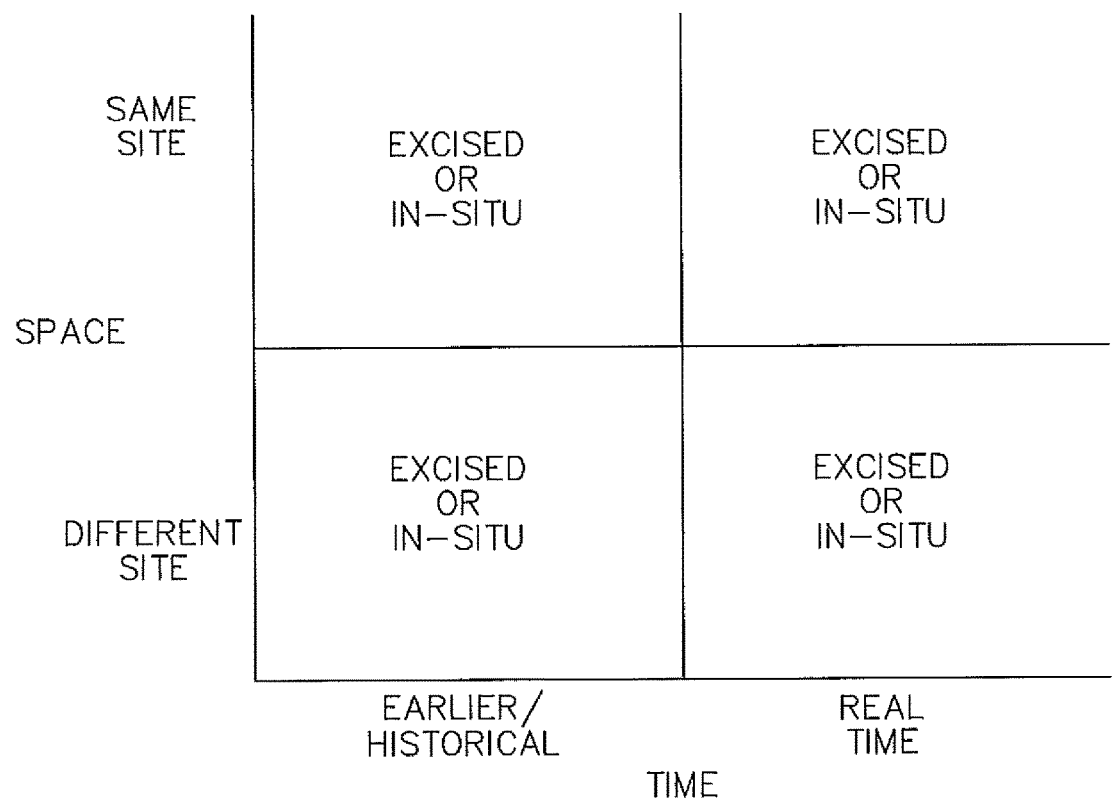

FIG. 15 is a diagram showing a number of options relating to the reference sample if the reference sample is from a person other than the person under evaluation. FIG. 16 is a diagram showing the same options on a spatial/temporal grid. The reference site may be a historical reference site, i.e. a site that had been previously evaluated when the tissue at the sight was known or believed to be healthy, with the results of the evaluation having been set aside for future use (node H). The historical reference site may be the same site as the site to be evaluated (node $H_S$). In the present context in which the reference site is a site on another person, "same site" means an anatomically analogous site on that different person or a sister site on that other person. Alternatively, the historical reference site may be a different site (node $H_D$). If the site is a different site it is preferably a sister site. Irrespective of whether the reference site is the same as the site currently under evaluation ($H_S$) or a different site ($H_D$), the sample can be excised from the reference site and then evaluated (nodes $H_{SE}$, $H_{DE}$) or can be subject to in-situ evaluation (nodes $H_{SI}$, $H_{DI}$).

Alternatively the reference site may be a site evaluated in real time, i.e. evaluated at essentially the same time as the target sample is being evaluated (node R). The real time reference site may be the same site as the site to be evaluated (node $R_S$) or may be a different site (node $R_D$). If the site is a different site it is preferably a sister site. Irrespective of whether the reference site is the same as the site currently under evaluation ($R_S$) or a different site ($R_D$), the reference sample can be excised from the reference site and then evaluated (nodes $R_{SE}$, $R_{DE}$) or can be subject to in-situ evaluation (nodes $R_{SI}$, $R_{DI}$).

As noted above when the reference site and the site of the tissue sample whose condition is sought are different sites, the site of the reference sample is preferably a sister site. A sister site is one whose tissue is known or believed to be healthy and whose tissue is believed to be a reasonably accurate surrogate for healthy tissue at the target site. Table 4 below shows one or more candidate sister sites for a number of target sites.

TABLE 4

| Target Site | Sister Site |
| --- | --- |
| Left or right heel | Opposite (right or left) heel |
| Sacrum | Gluteus, offset laterally from sacrum, or Sternum |
| Any site where the tissue condition is a condition of interest | Same site at an earlier time. |

As with the previously described methods, method 3 may disregard any component or portion of a detected dissimilarity that would be expected to occur if the skin were normal.

Method/Algorithm 4:

Method 4 is similar to method 2 in that both methods assess how one or more properties of reflected light changes over time. Method 4 differs from method 2 in that method 4 considers the intensity of reflected light at both a target site and a reference site (accounting, if necessary, for any differences in intensity between the light incident at those sites and the intensity of the light emitted at the source or sources of the light) whereas method 2 considers the properties of incident and reflected light at only a target site.

Figure 17:
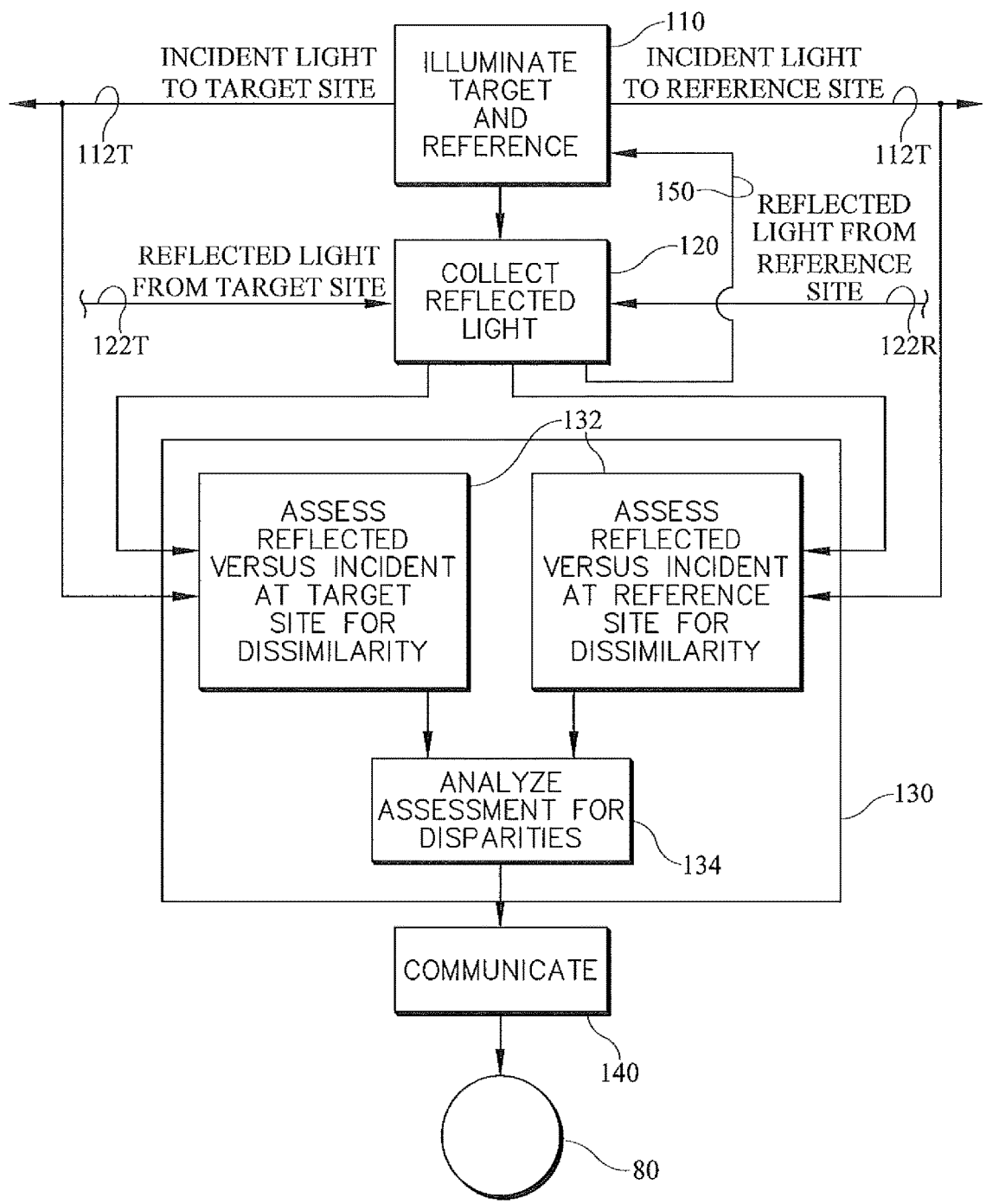
FIG. 17 is a block diagram showing a method (method 4) for detecting skin abnormalities such as pressure ulcers or precursors to pressure ulcers, the method involving an assessment over time of the relative intensity of light reflected from a target site and light reflected from a reference site.
Figure 18:
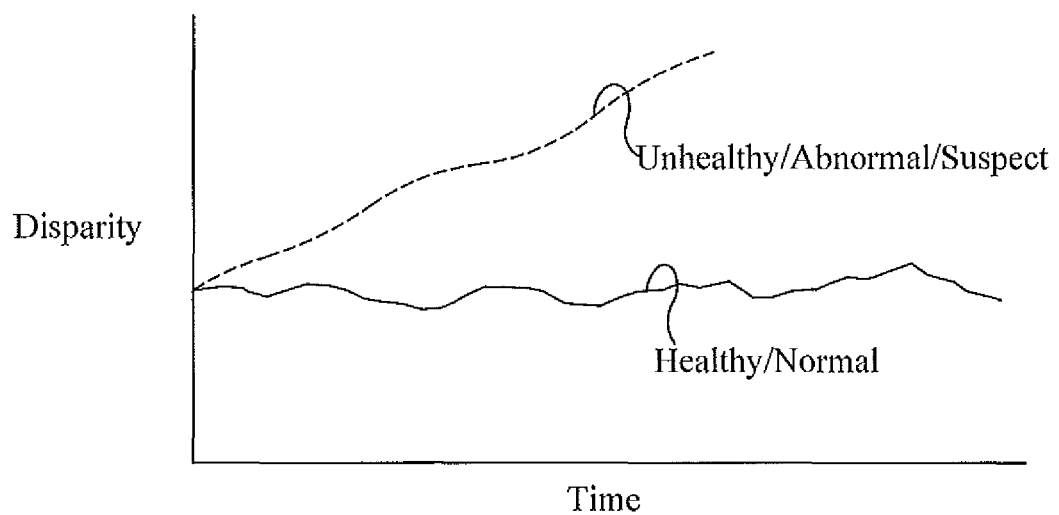
FIG. 18 is a graph showing substantially constant difference (solid line) which indicates healthy or normal tissue, or at least a difference that does not change over time, and a varying difference (broken line) which indicates an abnormality such as a pressure ulcer, or at least a region of skin that is suspect.

Referring to FIG. 17 method 4 is the same as the method of FIG. 11 with the addition of loop 150. The loop causes collection step 120 and evaluation step 130 to be repeated at discrete times, e.g. once every 30 minutes, or to be repeated substantially continuously. A substantially constant disparity difference (FIG. 18, solid line) indicates healthy or normal tissue, or at least a disparity that does not change over time. A change in the disparity (FIG. 18, broken line) indicates an abnormality such as a pressure ulcer, or at least a region of skin that is suspect. As with the previously described methods, method 4 may disregard any component or portion of a detected dissimilarity that would be expected to occur if the method were applied to normal skin. Method 4 may also disregard temporal differences that are attributable to causes other than development of a pressure ulcer.

Methods 5-8

The foregoing description of methods 1-4 employed a dissimilarity in light intensity as the indicator of the presence of a pressure ulcer or its precursors. Other optical properties may also be used. For example, methods 5-8 are similar to methods 1-4 but use dissimilarities in spectral content rather than dissimilarities in intensity as an indicator of tissue health. Method 5 inspects the reflected light for its spectral content and assesses that spectral content relative to the spectral content of the incident light at the same site as in method. 1. Method 6 is similar to method 5 but accounts for how the dissimilarity in spectral content progresses over time, as in method 2. Method 7 inspects the spectral content of light reflected from target and reference sites as in method 3. Method 8 is similar to method 7 but accounts for how the dissimilarity in spectral content progresses over time, as in method 4. The block diagrams for methods 5-8 are the same as those for methods 1-4. The eight methods are summarized in table 5:

TABLE 5

Summary of Methods

| | Parameter(s) compared | | | |
|---|---|---|---|---|
| | Single Site Incident vs. Reflected | | Target Site vs. Reference Site Reflected vs. Reflected | |
| | Time = Constant | Evaluated Over Time | Time = Constant | Evaluated Over Time |
| Dissimilarity in Intensity | Method 1 | Method 2 | Method 3 | Method 4 |
| Dissimilarity in Spectral Content | Method 5 | Method 6 | Method 7 | Method 8 |

Figure 19:
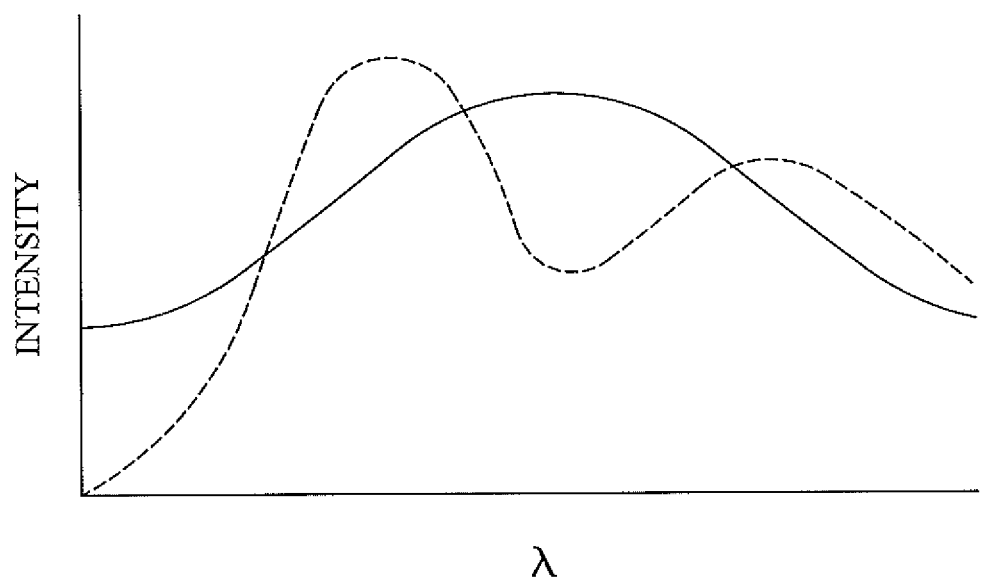
FIG. 19 is a graph illustrating reflected light intensities which do not exhibit the same intensity distribution over a defined wavelength band, e.g. the band bounded by $\lambda_{LOW}$ and $\lambda_{HIGH}$.

Whether the method inspects for intensity (methods 1-4) or spectral content (methods 5-8) is, to some extent, a matter of perspective. Referring to FIG. 6, for example, the difference between the solid and dashed lines can be viewed as a difference in intensity. The difference can also be viewed as a difference in spectral content because $B_1$ and $B_2$ do not exhibit the same intensity distribution over a defined wavelength band, e.g. the band bounded by $\lambda_{LOW}$ and $\lambda_{HIGH}$. The "spectral content" point of view may be more appropriate when the difference in intensity is not in the same direction across the entire spectral band of interest, as seen in FIG. 19.

The foregoing methods 1-8 have been described in connection with the architecture of FIGS. 1-2. The methods can also be carried out with other architectures. One such alternative architecture, illustrated in FIGS. 20-26, is one that employs optical fibers and windows in, for example, the support surface assembly 30, as described below.

The system of FIGS. 20-26 includes a caregiver interface with a display device 60 an input device 62, and a controller 58 having a processor 72 and a memory 70 as already described in connection with FIGS. 1-2. As with the system of FIGS. 1-2 other arrangements are possible and the controller may be dedicated to the pressure ulcer detection system or may be configured to control at least one function of the person support apparatus 10 and/or the support surface assembly 30 in addition to controlling the pressure ulcer detection system.

Figure 20:
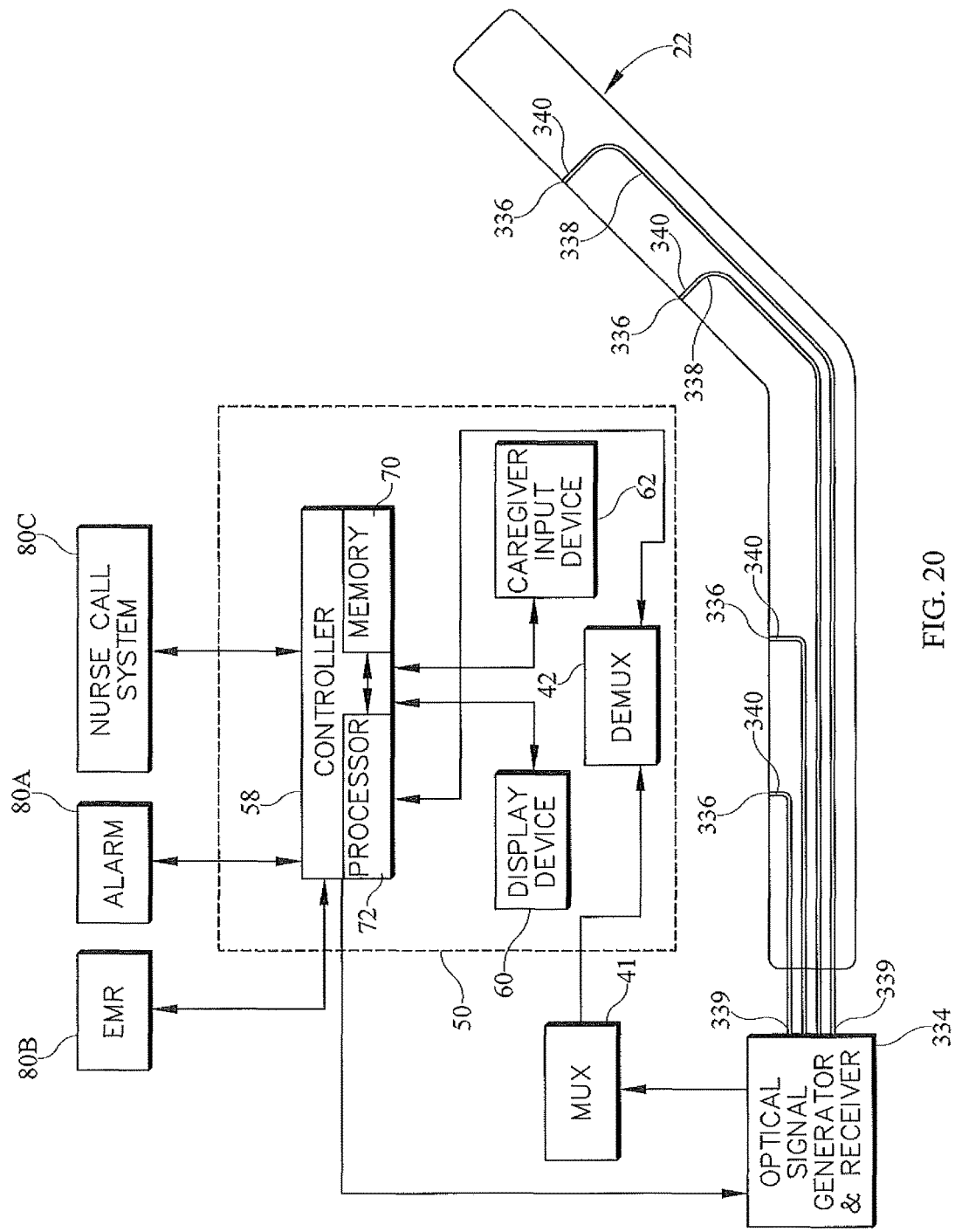
FIG. 20 is a view similar to that of FIG. 1 showing a system which employs an optical signal generator/receiver and optical fibers to carry out a method of detecting pressure ulcers or other skin abnormalities.
Figure 21:
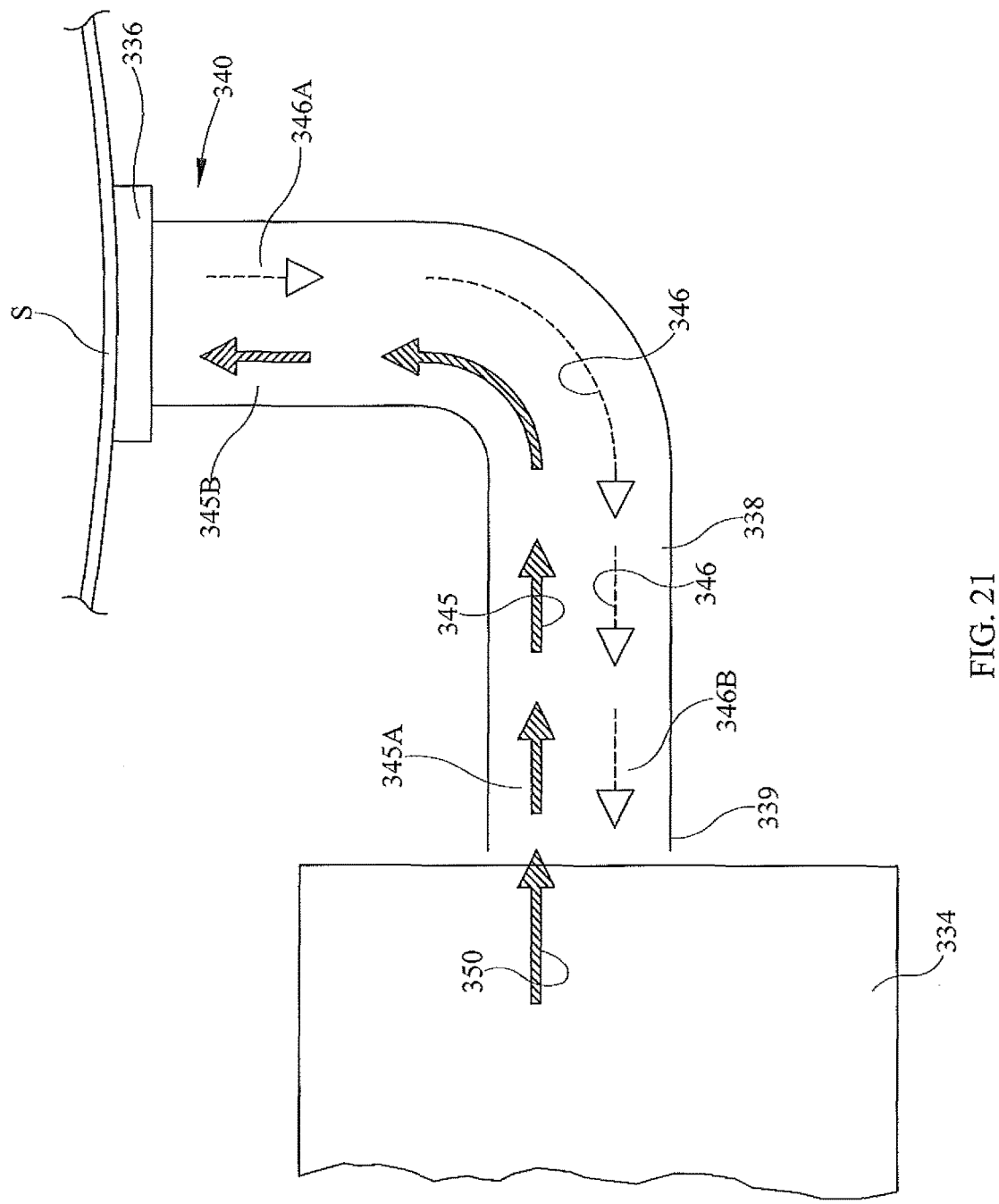
FIG. 21 is an enlarged view of a portion of FIG. 20.

The system of FIGS. 20-26 includes an optical signal generator and receiver 334 (also referred to as a signal generator/receiver). The system also includes at least one fiber 338 for conveying electromagnetic radiation generated by the signal generator from a first end 339 of the fiber to a second end 340 of the fiber and for conveying electromagnetic radiation from second end 340 to first end 339. As seen in FIG. 21 the output 350 of the signal generator is outgoing radiation 345 which is received by the first end 339 of fiber 338. At the second end 340 of fiber 338 the outgoing radiation is directed through window 336 (described in more detail below) to illuminate a portion of the occupant which overlies the window. Outgoing light 345 is therefore the light incident on the patient. When it is necessary to make a distinction between the outgoing radiation at the first and second ends 339, 340 of fiber 338 this specification and the drawings use reference numerals 345A and 345B respectively. Radiation reflected from the patient is captured at the second end 340 of fiber 338 and conveyed to the first end 339 where it is delivered to the signal generator/receiver. This radiation is referred to as incoming radiation 346. Incoming light 346 is the light reflected from the patient. When it is necessary to make a distinction between the incoming radiation at the second and first ends 340, 339 of fiber 338 this specification and the drawings use reference numerals 346A and 346B respectively. The signal generator and receiver 334 may be referred to as an optical signal generator and receiver even if the radiation it generates and receives is outside the visible portion of the spectrum. Similarly, fiber 338 may be referred to as an optical fiber even if the radiation conveyed therethrough is outside the visible portion of the spectrum. As explained in greater detail below in connection with FIGS. 25-26 a fiber 338 may be comprised of subfibers.

The support surface assembly also includes a region or window 336 which is transparent to desired wavelengths of electromagnetic radiation. Typically the support surface assembly will include multiple windows as seen in FIG. 20. Each optical fiber is arranged with its second end 340 adjacent to a window 336 so that radiation emitted from the second end of the fiber can illuminate a portion of the patient's body which overlies the window and so that the second end of the fiber can capture radiation reflected from the patient. At least some of the windows are positioned on the support surface assembly at places where the parts of a patient's body that are most susceptible to pressure ulcers will be located when the patient is occupying the bed. The positioning of the windows on the surface and their distribution on the surface take into account factors such as a distribution of patient sizes in the population and the postures that a patient would be expected to assume (e.g. prone, supine, lying on his or her side).

Each window 336 is transparent to the wavelengths it will receive from second end 340 of fiber 338 and to the wavelengths that will be reflected from the patient for conveyance back to the generator and receiver 334. If the support surface assembly is comprised of only mattress 20 as in FIG. 22, the at least one window 336 is window 336A in the upper surface of the mattress, which is the surface upon which the occupant rests. At least a portion of the optical fiber 338 is embedded in the mattress. The second end 340 of the optical fiber 338 is configured to emit light through window 336 so that the light illuminates a portion of the occupant that overlies the window. If the support surface assembly is comprised of both mattress 20 and topper 22 as in FIG. 23, at least a portion of the optical fiber can be embedded in the topper, and the at least one transparent window 336 is window 336B in the upper surface of the topper, which is the surface in contact with the occupant. Second end 340 of the optical fiber 338 is configured to emit light through window 336B so that the light illuminates a portion of the occupant that overlies the window. If the support surface assembly is comprised of both mattress 20 and topper 22 as in FIG. 24, at least a portion of the optical fiber can be embedded in the mattress, and the at least one window 336 is the combination of window 336A, window 336B, and window 336C in the lower surface of the topper. In this alternative, second end 340 of the optical fiber 338 is configured to emit light through window 336 so that the light illuminates a portion of the occupant that overlies the window.

As seen best in FIGS. 21-22, first end 339 of each fiber 338 is arranged to communicate with the signal generator and receiver 334. In particular the first end is arranged to receive radiation from the signal generator/receiver and to deliver the reflected radiation to the generator/receiver. Second end 340 of fiber 338 is arranged to direct the radiation through window 336 in a first direction, specifically toward an occupant tissue site S. Second end 340 is also arranged to capture radiation which reflects from an occupant tissue site overlying the window and passes back through the window in a second direction opposite to the first direction. The first end is also arranged to deliver the reflected radiation to the generator/receiver.

The first end 339 of the optical fiber 338 is supplied with electromagnetic radiation by optical signal generator and receiver 334. The optical signal generator and receiver 334 is configured to communicate with controller 58. The controller 58 controls the optical signal generator and receiver 334 and provides a control signal to initiate transmission of a portion of electromagnetic spectrum through optical fiber 338 and the transparent region 336 onto the patient's skin. The radiation, or at least some of the radiation, is reflected from the patient, back through window 336, through the fiber 338 and to generator and receiver 334. In the case where there is more than one fiber, the optical signal generator and receiver 334 sends light received from first end 339 of the optical fibers 338 to a multiplexer 41 to multiplex the signals. The multiplexed signal is demultiplexed by a demultiplexer 42. In another embodiment the multiplexed signal sent by the multiplexer 41 is logically de-multiplexed by the processor 72 instead of by using a physical demultiplexer.

In operation controller 58 provides a control signal to the optical signal generator and receiver 334 to transmit at least a portion of the electromagnetic spectrum through the optical fibers 338 and through window 336 and onto the patient. Light reflected from the patient is captured by the optical fibers 338 and transmitted to the optical signal generator and receiver 334. The optical signal generator and receiver 334 transmits light received from the optical fibers 338 to the multiplexer 41. The multiplexer 41 multiplexes signals received from the various optical fibers 338 before transmitting them to a demultiplexer 42 which is shown as a component of caregiver interface 50. The demultiplexer 42 separates out the individual signals and supplies the individual signals to processor 72. In one variant the signal received through the transparent regions 336 is transmitted by the optical fibers 338 directly to the multiplexer 41 instead of going through the optical signal generator and receiver. The processor 72 includes signal conditioning functionality to condition signals received through the optical fibers 338.

Processor 72 is adapted to assess, based on the optical properties of the outgoing radiation 345 and the optical properties of the incoming radiation 346, whether or not the tissue site is healthy. Specifically, the processor executes an algorithm, such as methods 1-8, that uses the outgoing and incoming radiation properties to assess tissue health. As already described in connection with FIGS. 1-2, if the processor determines that tissue is unhealthy, for example that it contains a pressure ulcer or other wound, the processor activates alarm 80A and/or communicates with nurse call system 80C and/or communicates with an EMR database 80B.

Figure 25:
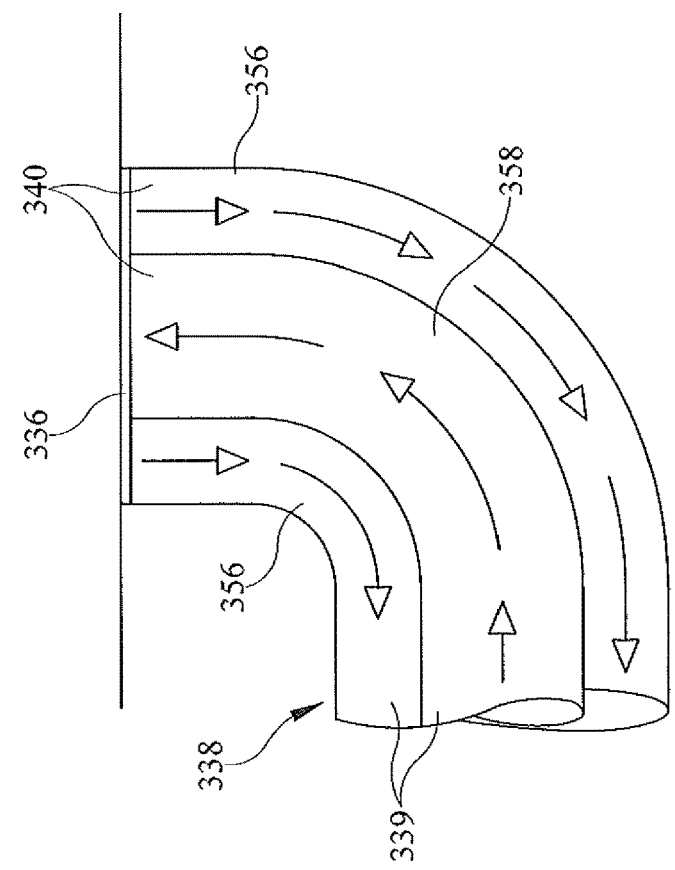
FIG. 25 is an elevation view showing an optical fiber comprised of subfibers arranged coaxially.
Figure 33:
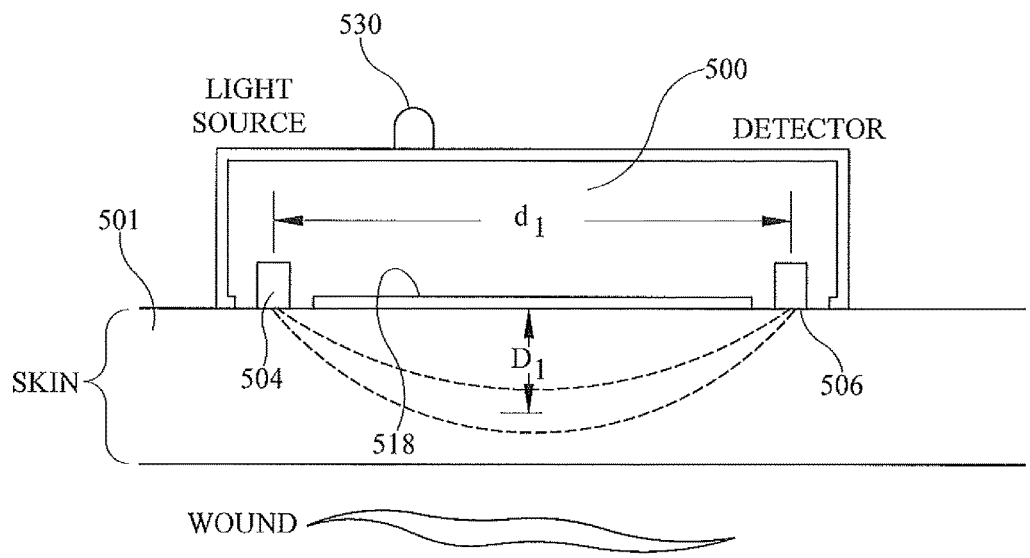
FIGS. 33-34 are schematic views of a device, exemplified as a noninvasive wearable module, which detects wounds such as pressure ulcers, or precursors to such wounds by optically monitoring for one or more biomarkers, associated with the wounds.
Figure 34:
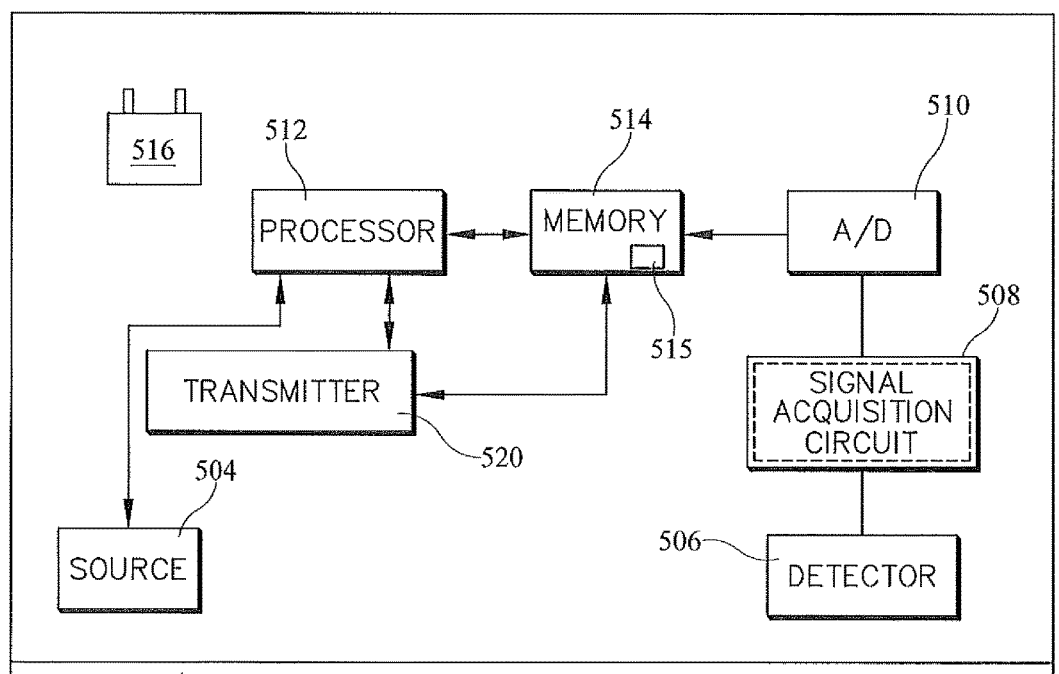

FIG. 25 shows a segment of an optical fiber 338 comprised of coaxial subfibers 356, 358. One of the subfibers, for example subfiber 358, is an outgoing fiber. The other, in this case subfiber 356, is an incoming fiber. Fiber 358 receives light at its first end 339 from a source thereof such as generator and receiver 334 and conveys the light to its second end 340. The light is directed from the second end and through windows 336 to illuminate the skin of the person supported by the support surface assembly. Light reflected from the patient traverses the window and is captured by light return subfiber 356 at its second end. Subfiber 356 conveys the light to its first end and delivers it to the generator and receiver. Subfibers 356 and 358 are arranged such that their second ends 340 each occupy a portion of window 336 as shown in FIG. 33S.

Figure 26:
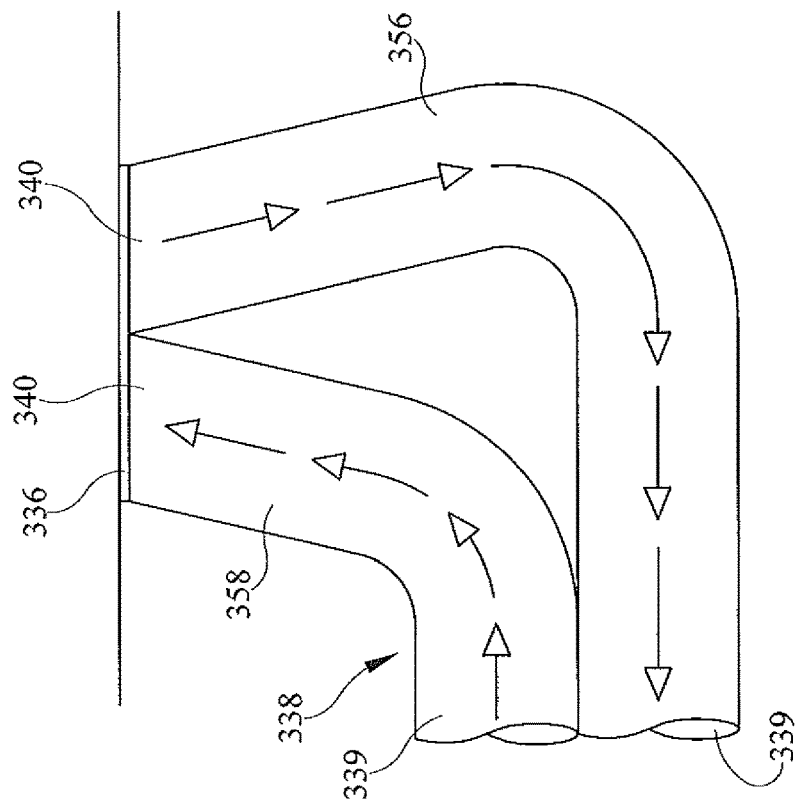
FIG. 26 is an elevation view showing an optical fiber comprised of subfibers arranged non-coaxially.

FIG. 26 shows a segment of an optical fiber 338 comprised of non-coaxial subfibers 356, 358. One of the subfibers, for example subfiber 358, is an outgoing fiber. The other, in this case subfiber 356, is an incoming fiber. Subfiber 358 receives light at its first end 339 from a source thereof such as generator and receiver 334 and conveys the light to its second end 340. The light is emitted from the second end and through window 336 to illuminate the skin of the person supported by the support surface assembly. Light reflected from the patient traverses the window and is captured by light return subfiber 356 at its second end. Subfiber 356 conveys the light to its first end and delivers it to the generator and receiver. Fibers 356 and 358 are arranged such that their second ends 340 each occupy a portion of the window 336 as shown in FIG. 26.

Figure 27:
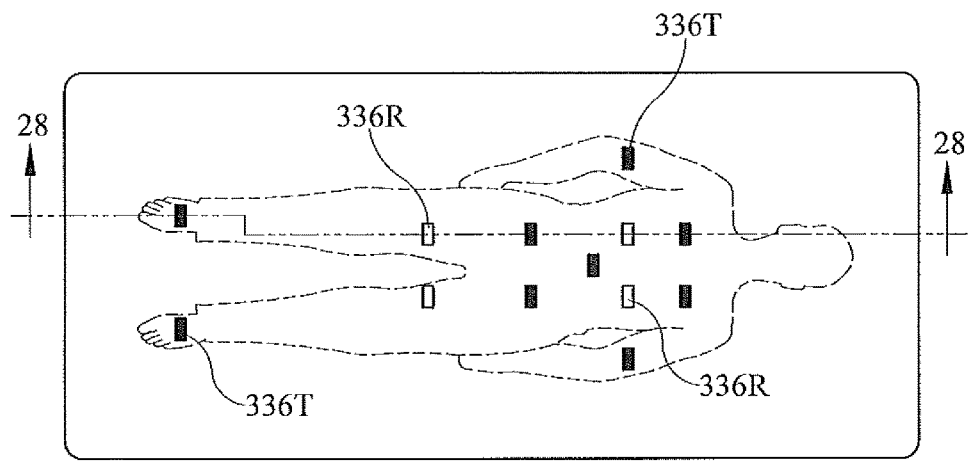
FIG. 27 is a plan view showing a specific embodiment of the system of FIGS. 21-22.
Figure 28:
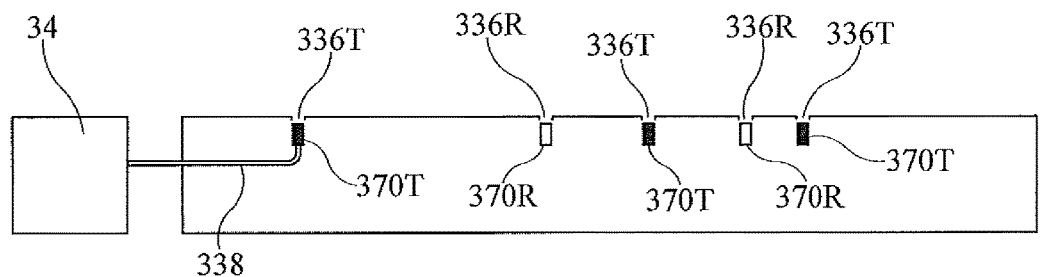
FIG. 28 is a side elevation view taken in the direction 28-28 of FIG. 27.
Figure 29:
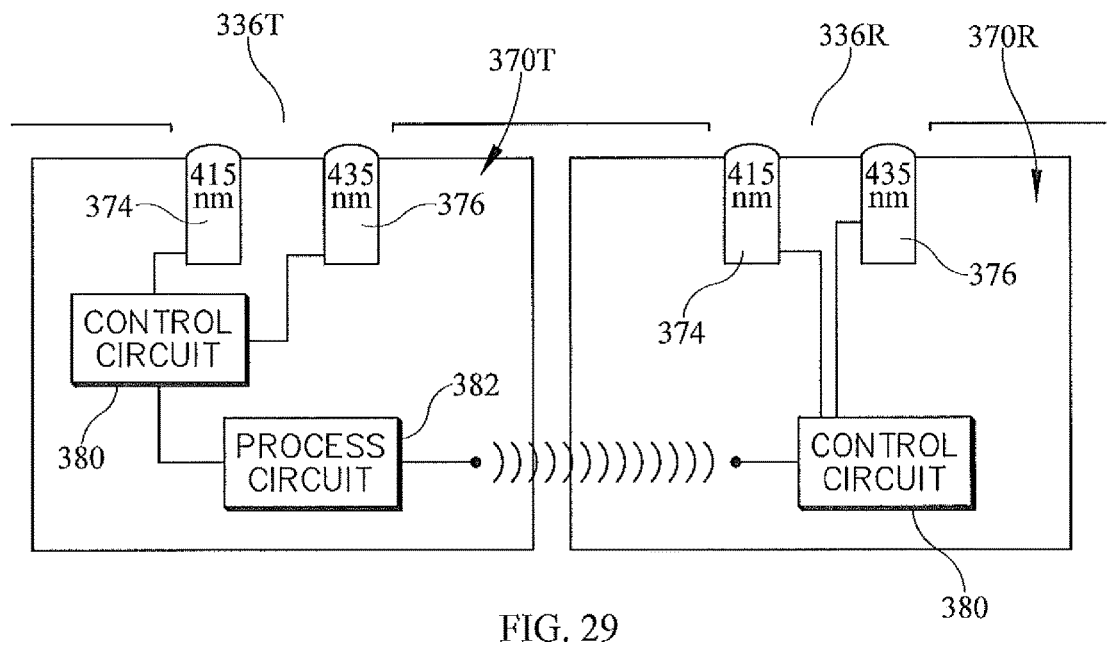
FIG. 29 is a schematic view of target and reference detector units used in the embodiment of FIGS. 27-28.

FIGS. 27-29 illustrate a specific example of using the architecture of FIG. 20 with one of the methods 1-8, specifically method 3 in which dissimilarities between the tissue at one or more target sites and the tissue at one or more reference sites is used to indicate the presence of a pressure ulcer or its precursors. The specific example also employs light of two different discrete wavelengths, 415 nm and 435 nm, as in the example of method 3 and the graph of FIG. 12.

FIG. 27 is a plan view of a mattress showing an approximate outline of a supine occupant. FIG. 28 is a view in the direction 28-28 of FIG. 27. The mattress includes a number of transparent windows 336T, 336R. In FIGS. 27-28 some of the windows 336R are intentionally positioned so that the overlying tissue will be at a site on the occupant's body that is not highly susceptible to the development of pressure ulcers. The window (or windows) so positioned and the corresponding site on the occupant's body may be referred to as a reference window and a reference site. The fibers 338 that extend from the signal generator/receiver to a reference window are reference fibers. A reference detector unit 370R, is positioned or otherwise associated with at each reference window.

The other windows are positioned at places on the surface where the parts of a patient's body that are most susceptible to pressure ulcers will be located when the patient is occupying the bed. The windows so positioned and the corresponding sites on the occupant's body may be referred to as target windows 336T and target sites. The fibers 338 that extend from the signal generator/receiver to a target window are target fibers. A target detector unit 370T, is positioned at or otherwise associated with each target window. The processor is adapted to assess whether or not the tissue site is healthy, based on dissimilarities between the spectral content of the radiation delivered by the reference optical fiber and the spectral content of the radiation delivered by the target optical fiber.

Each target unit and each reference unit includes a 415 nm narrow band illuminator/receiver 374 and a 435 nm narrow band illuminator/receiver 376. Each illuminator/receiver can be commanded to emit narrow bandwidth radiation at its respective wavelength in order to illuminate the overlying tissue sample (i.e. the occupant's tissue). Each illuminator/receiver can also receive radiation reflected from the tissue site. A control circuit 380 is in communication with the illuminator/receiver. A processing circuit 382 on each target unit 370T communicates nonwirelessly with the control circuit on the same target unit and communicates wirelessly with the control circuit on at least one of the reference units 370R.

The arrangement of FIG. 29 is only one of many substantially equivalent arrangements that can be employed. For example arrangements with a single, shared control circuit or with the processing circuit on the reference unit rather than on the target unit may be satisfactory.

Figure 30:
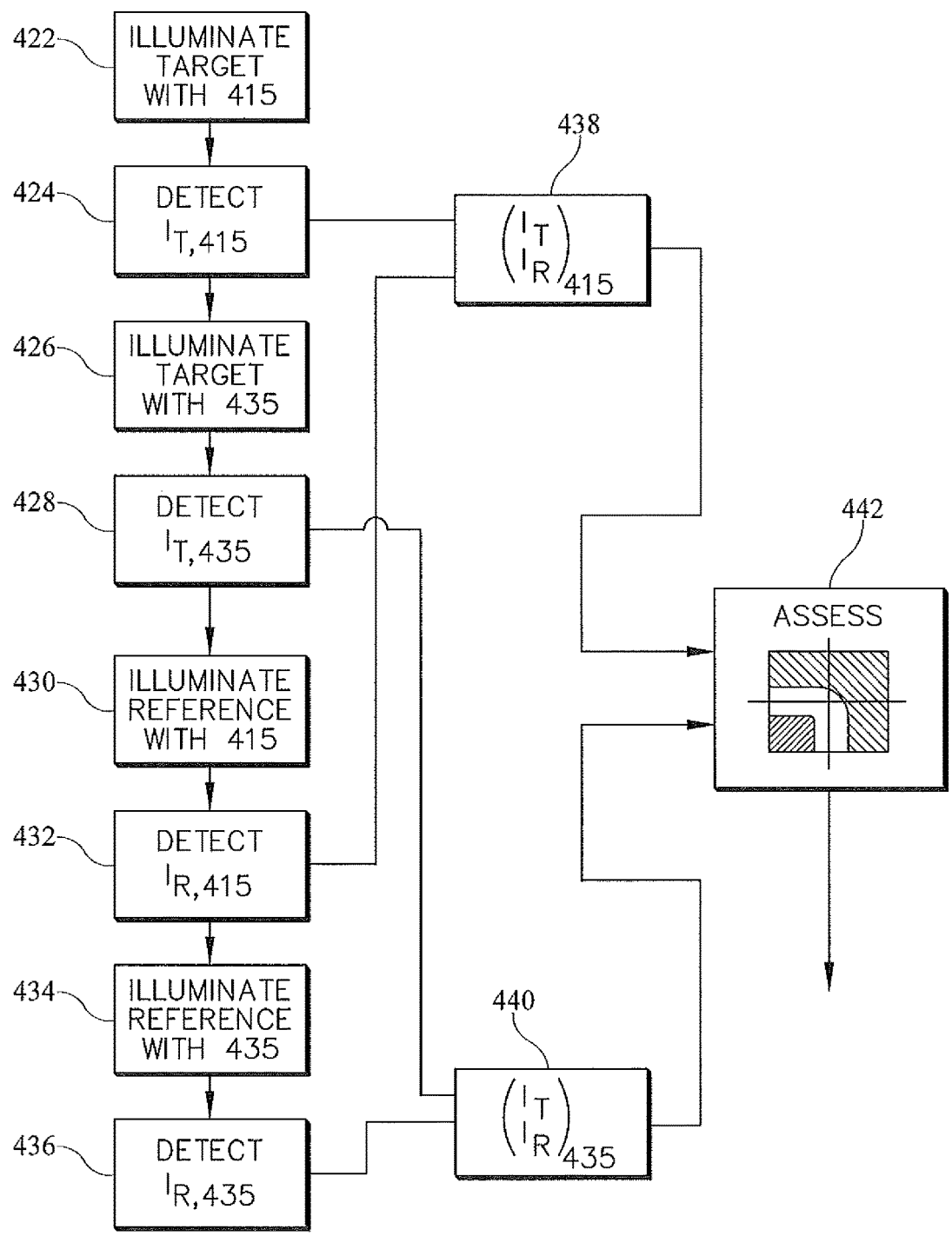
FIG. 30 is a block diagram illustrating a specific example of a method of pressure ulcer detection carried out with the embodiment of FIGS. 27-28.

Referring additionally to FIG. 30, in operation the control circuits 380 command the illuminator/receivers to illuminate the target sites and reference sites with which they are aligned (blocks 422, 426, 430, 434). Each target unit control circuit 380 monitors the intensity of radiation reflected from its target site (blocks 424, 428) and communicates that intensity to the processing circuit 382. The reference unit control circuit monitors the intensity of radiation reflected from its reference site (blocks 432, 436) and makes that intensity available to the processing circuit. Each processing circuit determines the ratios $(I_{TGT}/I_{REFERENCE})_{415}$ and $(I_{TGT}/I_{REFERENCE})_{435}$ (blocks 438, 440). The processing circuit uses the determined ratios to assess the health of the tissue at each of the target sites (block 442). One method of assessment is to use the relationship of FIG. 12. The outcome of the assessment, including warnings when appropriate, can be provided either continuously, intermittantly (e.g. once every 30 minutes) or only when the system detects unhealthy tissue or conditions that are precursors to unhealthy tissue.

In the foregoing example the pressure ulcer prediction system is illustrated in the context of a mattress. That is, at least some of the components are a part of the mattress or are used in conjunction with the mattress. More generally, the system is useable as part of or in conjunction with other articles. These include bed linens, wraps that wrap around a portion of a patient's limb, patches that rest on the mattress between the mattress and the patient, patches that adhere to the patient, and garment or garment-like articles such as booties.

The processor 72 also has the capability to identify the patient supported by the support surface assembly, for example from an RFID tag worn by the patient. Such identification allows patient specific data to be conveyed to or retrieved from the electronic medical record (EMR). As a result any detection of a pressure ulcer can be easily and automatically associated with the medical record of the patient.

Figure 31:
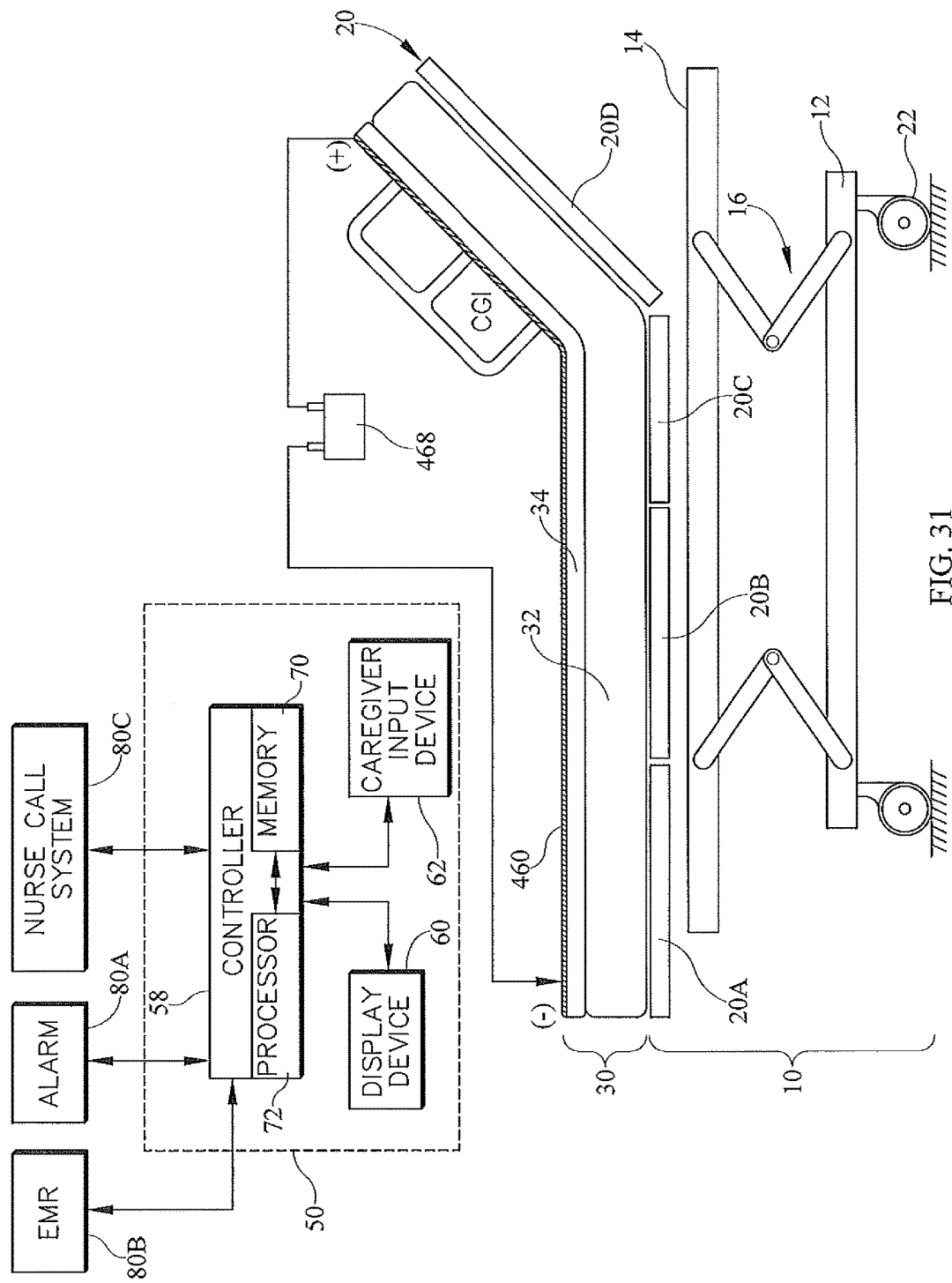
FIG. 31 is a view similar to that of FIG. 1 showing a system which employs a dielectric material to carry out a method of detecting pressure ulcers or other skin abnormalities.
Figure 32:
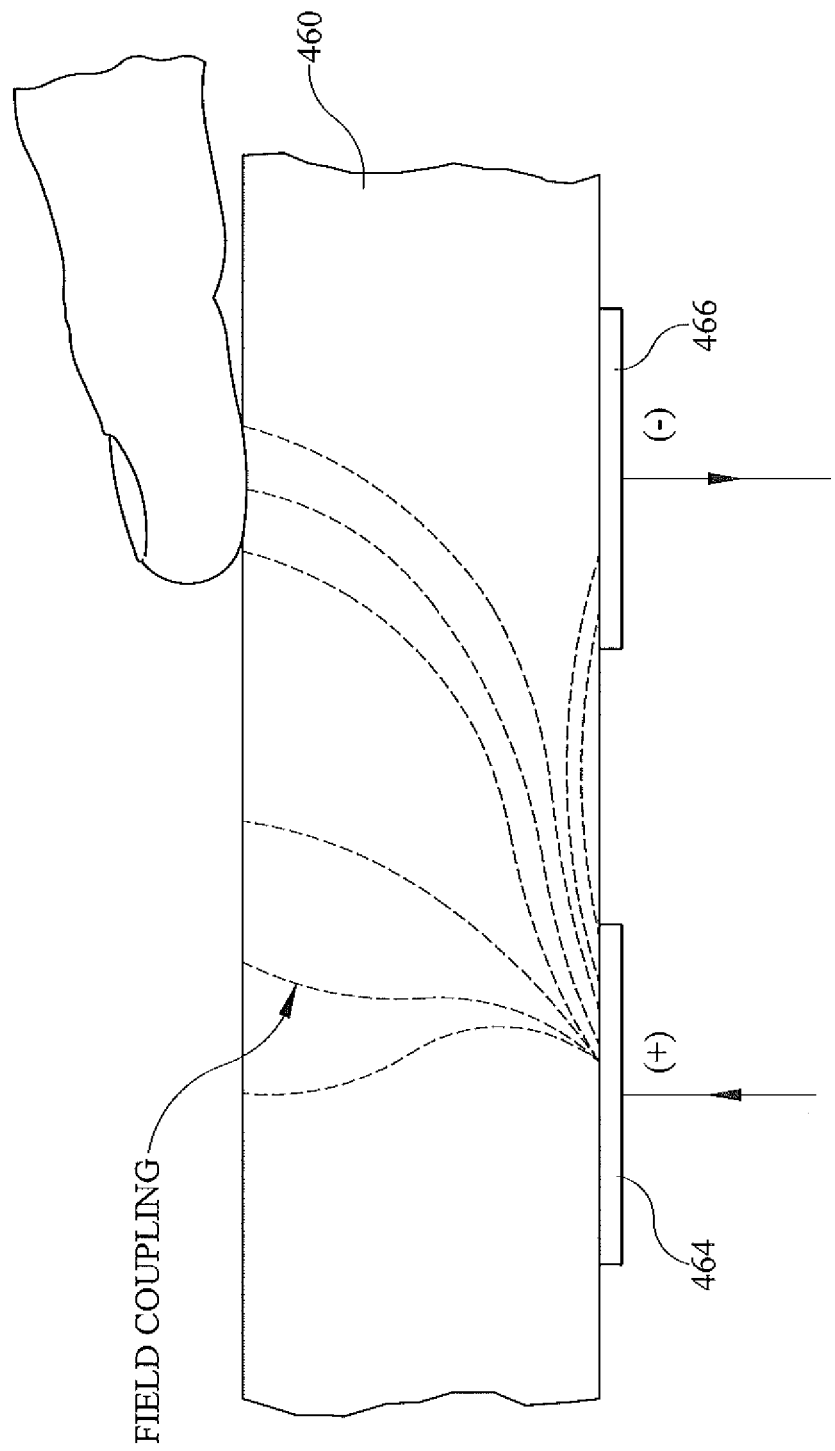
FIG. 32 is an enlarged view of a portion of FIG. 31 illustrating a variation in the electric potential between electrodes of the embodiment of FIG. 31 due to field coupling as a result of a person being in contact with the dielectric material.

FIGS. 31-32 show another embodiment of a system to detect pressure ulcers on a person supported by a person support apparatus or framework 10. The person support surface assembly 30 includes a mattress 20 and a topper 22. The topper includes a dielectric assembly comprising a dielectric material 460 such that at least a portion of the dielectric material 460 is in contact with a person supported by the mattress topper 22. In another variant the dielectric material 460 may be incorporated in the mattress 32, in which case the mattress is used without a topper. In another variant a layer or sheet of dielectric material may be placed on top of the person support surface assembly. The dielectric assembly also includes positive and negative electrodes 464, 466 which connect the dielectric material to a source of electric potential, such as battery 468.

Referring to FIG. 32 a person in contact with the dielectric material 460 causes variation in the electric potential between the electrodes due to field coupling. Furthermore the system to detect pressure ulcers is configured to distinguish between changes in electrical potential between positively and negatively charged electrodes when the dielectric material is in contact with skin susceptible to pressure ulcers and healthy skin. In one embodiment the controller 58 is configured to determine the difference in potential between positively and negatively charged electrodes when the dielectric material is in contact with skin susceptible to pressure ulcers and healthy skin because skin susceptible to pressure ulcers retains fluid or displays edema. The presence of fluid in certain areas of skin allows the controller to differentiate between healthy skin and skin displaying edema. The processor 72 is configured to locate the local response of the patient's skin with respect to adjacent regions of the patient's skin based on change in potential between the various positively and negatively charged electrodes and identify areas of the patient's skin susceptible to pressure ulcers. If the processor determines that tissue is unhealthy, for example that it contains a pressure ulcer or other wound, the processor activates alarm 80A and/or communicates with nurse call system 80C and/or communicates with an EMR database 80B.

FIGS. 33-36 show and describe the operation of a device, exemplified as a noninvasive wearable module 500, which detects wounds such as pressure ulcers, or precursors to such wounds by optically monitoring for one or more chemicals, specifically one or more biomarkers, associated with the wounds. A biomarker is "a characteristic that is objectively measured and evaluated as an indicator of normal biological processes, pathogenic processes or pharmacologic responses to a theraputic intervention." ("Biomarkers and surrogate endpoints: Preferred definitions and conceptual framework", Clinical Pharmacology & Theraputics, Vol. 69 No. 3, March 2001) Biomarkers include chemicals and other biophysical parameters, for example electrical properties of the tissue. The presence or absence of a biomarker is determined by changes in an optical property of light signals as a result of the signal having propagated through a patient's tissue. The optical property is a property that is affected by chemicals as a result of the light having propagated through the tissue and having encountered the chemicals. Biomarkers have superior sensitivity and specificity for deep tissue wound detection. Although several biomarkers have been studied, two compounds that have received much attention are CPK or creatine phosphokinase (a breakdown product of muscle tissue) and IL-1a, or interleukin 1-alpha, a marker of early stage inflammation.

Module 500 is attached to a patient's skin 501 at a target site. The module includes a light source 504 and an optical detector 506. The module also includes a signal acquisition circuit 508, an analogue to digital (AD) converter 510, a processor 512 and a memory 514. The memory is used to store a signal analysis algorithm 515 and other information such as signals detected by the optical detector and results of analysis carried out on the detected signal. The module also includes a battery 516 to power the electrical components of the module and an adhesive 518 to mount the sensor to the skin. A transmitter 520 is provided to enable communication between the module and remote devices.

Figure 35:
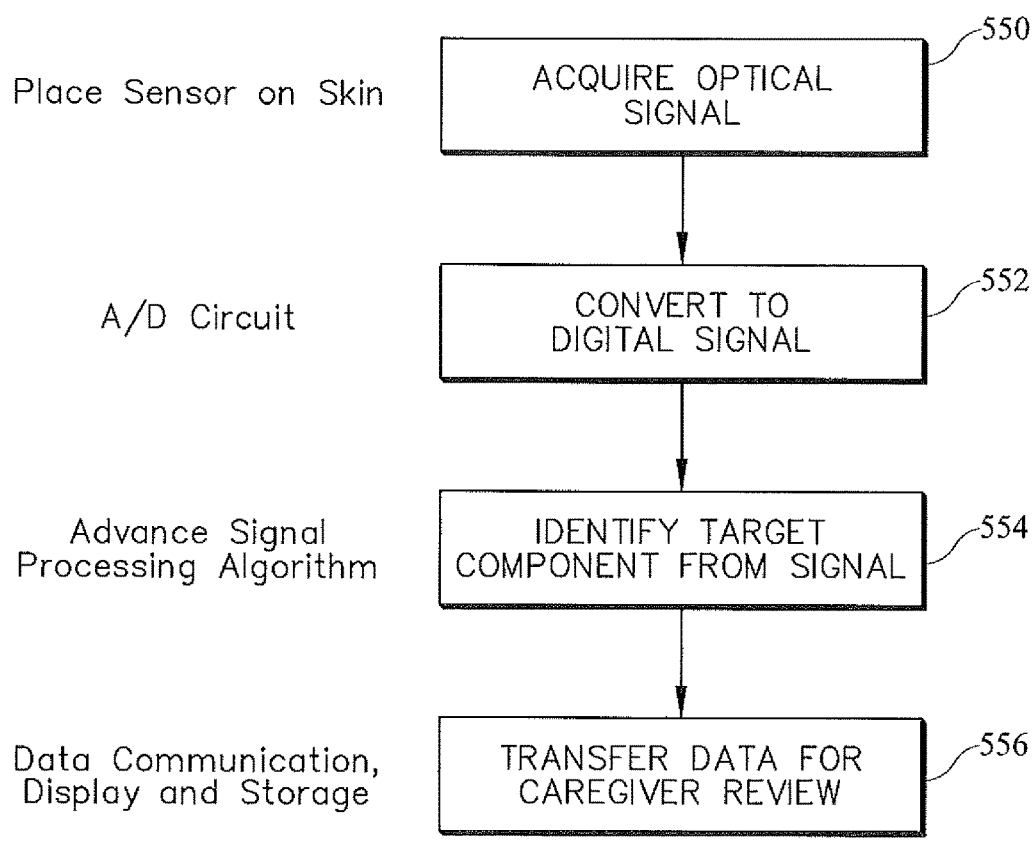
FIG. 35 is a schematic view of operation of the device of FIGS. 33-34.

In operation, light from light source 504 passes through the skin tissue and is received and detected by light detector 506 (Block 550 of FIG. 35). The depth $D_1$ at which the tissue is inspected depends on the separation distance $d_1$ between the light source and the detector. The data acquisition circuitry acquires the optical data and converts it to an electrical signal. The AD converter 510 digitizes the data (block 552) for further processing.

The processor 512 executes the signal analysis algorithm 515. The signal analysis algorithm is applied to the acquired signal to identify the change or difference in an optical property of the acquired signal relative to the optical property of the signal emitted by the light source (block 554). As used herein, the change or difference in an optical property is not limited to a simple arithmetic difference but could be represented by, for example, a ratio. The change is due to and therefore indicative of the biochemical which, in turn, is indicative of a pressure ulcer or other wound. For example the change may be a change in light intensity at a given wavelength or may be a change in the spectral content of the light. The algorithm may employ simple threshold comparisons or may use something more complex, such as Principal Component Analysis (PCA) to analyze the spectrum of the acquired light signal.

Figure 36:
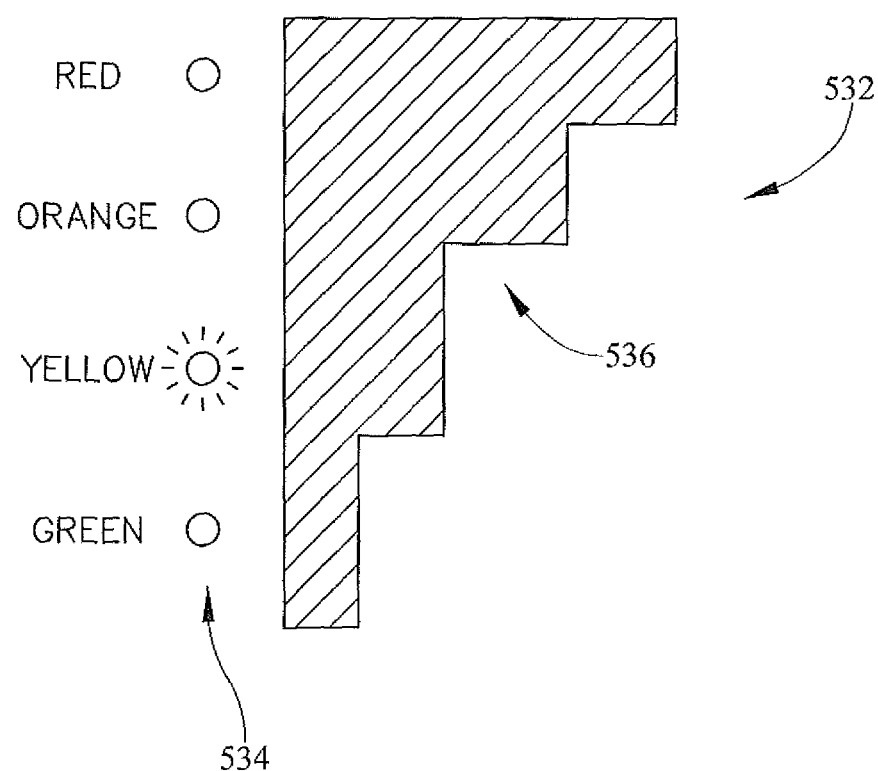
FIG. 36 is a schematic view of a graduated wound severity indicator in the form of an array of differently colored LED's alongside a stepped severity scale.

The module provides for continuous monitoring of the target site and therefore immediate sampling and analysis of the biomarker compounds as they accumulate. When a biomarker of interest is detected its presence can be revealed by a simple binary output in which one of two states of a device (e.g. a light emitting diode (LED) 530 (FIG. 60) reveals the presence of a biomarker (light on) or the absence of a biomarker (light off). In another variant seen in FIG. 36 a graduated indication of wound severity is provided in which the wound severity is indicated by the concentration of the biomarker, and the concentration of the biomarker is indicated by the difference in intensity, spectral content, or other optical property. The example of FIG. 36 shows a graduated indicator 532 in the form of an array 534 of differently colored LED's alongside a stepped severity scale 536.

The LED 530 and graduated indicator provide a local indication. Additionally or alternatively transmitter 520 communicates wound status to a remote device such as a computer or handheld device (block 556).

Because the module 500 is a continuous monitoring device, tissue status as a function of time can be recorded for historical trend review. This historic record of biochemical levels, along with outcomes, can be used to refine the algorithm.

The use of the terms "a" and "an" and "the" and similar referents in the context of describing the subject matter (particularly in the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Variations of the embodiments described herein will be apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

The invention claimed is:

1. A pressure ulcer detection system comprising:
   a support surface assembly including multiple transparent windows;
   a signal generator/receiver;
   an optical fiber embedded at least in part in the support surface assembly for conveying outgoing radiation from the signal generator/receiver to the windows thereby illuminating a tissue site which overlies each window and for conveying incoming radiation reflected from the tissue site and through the window back to the generator/receiver;
   a controller in communication with the signal generator/receiver, the controller comprising a processor adapted to assess health status of tissue at the tissue site based on a property of at least one of the outgoing radiation and the incoming radiation, and to communicate an outcome of the assessment to a destination;
   wherein at least some of the windows are target windows which are positioned on the support surface assembly where parts of a patient's body that are most susceptible to pressure ulcers will be located when the patient is occupying the support surface assembly.

2. The pressure ulcer detection system of claim 1 wherein fewer than all of the windows are target windows, and windows other than the target windows are reference windows which are positioned on the support surface assembly where parts of the patient's body that are not susceptible to pressure ulcers will be located when the patient is occupying the support surface assembly.

3. The pressure ulcer detection system of claim 1 wherein the parts of the patient's body that are most susceptible to pressure ulcers are target sites and wherein the processor is adapted to assess tissue health based on the property of the radiation incident on tissue at the target site and the property of radiation reflected from the tissue at the target site at substantially the same time.

4. The pressure ulcer detection system of claim 1 wherein the parts of the patient's body that are most susceptible to pressure ulcers are target sites and wherein the processor is adapted to assess tissue health based on changes over time in a relationship between the property of the radiation incident on tissue at the target site and the property of radiation reflected from the tissue at the target site.

5. The pressure ulcer detection system of claim 2 wherein the parts of the patient's body that are most susceptible to pressure ulcers are target sites, the parts of the patient's body that are not susceptible to pressure ulcers are reference sites and wherein the processor is adapted to assess tissue health based on the property of the radiation reflected from tissue at the target site and the property of the radiation reflected from the tissue at the reference site at substantially the same time.

6. The pressure ulcer detection system of claim 2 wherein the parts of the patient's body that are most susceptible to pressure ulcers are target sites, the parts of the patient's body that are not susceptible to pressure ulcers are reference sites and wherein the processor is adapted to assess tissue health based on changes over time in a relationship between the property of the radiation reflected from tissue at the target site and the property of the radiation reflected from the tissue at the reference site.

7. A method of pressure ulcer detection comprising:
illuminating a target site with incident radiation having at least one property;
detecting the at least one property of radiation reflected from the target site;
conducting an evaluation to identify whether a dissimilarity is present in the property of the source radiation relative to the property of the reflected radiation; and
communicating an outcome of the step of conducting an evaluation to a destination.

8. The method of claim 7 wherein the step of conducting an evaluation considers changes over time in a relationship between the property of the incident radiation and the property of the reflected radiation.

9. A method of pressure ulcer detection comprising:
illuminating a target site with incident radiation;
illuminating a reference site with incident radiation;
detecting at least one property of radiation reflected from the target site;
detecting at least one property of radiation reflected from the reference site;
conducting an evaluation to identify whether a relationship between the property of the radiation reflected from the target site and the property of the radiation reflected from the reference site changes over time; and
communicating an outcome of the step of conducting an evaluation to a destination.

* * * * *